United States Patent
Gallagher et al.

(10) Patent No.: US 10,923,227 B2
(45) Date of Patent: Feb. 16, 2021

(54) TRACKING PROGRAM INTERFACE

(71) Applicant: Episode Solutions, LLC, Nashville, TN (US)

(72) Inventors: Thomas A. Gallagher, Nashville, TN (US); Kathryn Douglas, Nashville, TN (US)

(73) Assignee: Episode Solutions, LLC, Nashville, TN (US)

( * ) Notice: Subject to any disclaimer, the term of this patent is extended or adjusted under 35 U.S.C. 154(b) by 0 days.

(21) Appl. No.: 16/052,351

(22) Filed: Aug. 1, 2018

(65) Prior Publication Data

US 2019/0043613 A1 Feb. 7, 2019

Related U.S. Application Data

(60) Provisional application No. 62/540,931, filed on Aug. 3, 2017.

(51) Int. Cl.
*G16H 40/20* (2018.01)
*G08B 25/10* (2006.01)
*G16H 40/67* (2018.01)
*G16H 10/60* (2018.01)
(Continued)

(52) U.S. Cl.
CPC ......... *G16H 40/20* (2018.01); *G08B 21/0423* (2013.01); *G08B 25/10* (2013.01); *G16H 10/60* (2018.01); *G16H 40/67* (2018.01); *G16H 80/00* (2018.01)

(58) Field of Classification Search
None
See application file for complete search history.

(56) References Cited

U.S. PATENT DOCUMENTS 5,497,149 A * 3/1996 Fast ............... B60R 25/102
340/426.19
6,313,760 B1 * 11/2001 Jones ............... G08G 1/123
340/989

(Continued)

OTHER PUBLICATIONS

Boulos, et al., "Real-time locating systems (RTLS) in healthcare: a condensed primer," International Journal of Health Geographics, vol. 11, No. 1, Jun. 28, 2012, 8 pgs.

(Continued)

*Primary Examiner* — Curtis J King
(74) *Attorney, Agent, or Firm* — Waller Lansden Dortch & Davis, LLP; Matthew C. Cox

(57) ABSTRACT

Computer systems and methods are provided for tracking a user. Data for a first user, including a first identifier associated with the first user, is received. A first tracking program for the first user that includes a first identifier associated with the first user, a first indicated area for a first user device, associated with the first user and a first time period when the first user is scheduled to be located within the first indicated area is generated and stored. At a first time that corresponds to the first time period, a position detection system determines a first determined position of the first user device. The first determined position of the first user device is compared with the first indicated area. In accordance with a determination that the first determined position of the first user device does not correspond to the first indicated area a first tracking alert is transmitted.

19 Claims, 44 Drawing Sheets

(51) Int. Cl.
*G16H 80/00* (2018.01)
*G08B 21/04* (2006.01)

(56) References Cited

U.S. PATENT DOCUMENTS

| | | | | |
|---|---|---|---|---|
| 6,363,323 B1* | 3/2002 | Jones | G06Q 10/08 | |
| | | | 340/989 | |
| 7,379,812 B2* | 5/2008 | Yoshioka | G01C 21/32 | |
| | | | 340/995.19 | |
| 7,913,179 B2* | 3/2011 | Sheha | H04L 51/04 | |
| | | | 701/532 | |
| 9,485,206 B2* | 11/2016 | Day, II | H04L 51/16 | |
| 10,204,499 B1* | 2/2019 | Newstadt | G08B 21/0269 | |
| 10,237,280 B2* | 3/2019 | Day, II | H04L 63/101 | |
| 10,522,188 B2* | 12/2019 | Rothschild | G06K 9/00892 | |
| 2002/0067272 A1* | 6/2002 | Lemelson | G08B 21/0233 | |
| | | | 340/573.4 | |
| 2003/0016804 A1* | 1/2003 | Sheha | G01C 21/26 | |
| | | | 379/201.06 | |
| 2003/0172940 A1* | 9/2003 | Rogers | A61B 5/0031 | |
| | | | 128/899 | |
| 2004/0019501 A1 | 1/2004 | White et al. | | |
| 2004/0021567 A1 | 2/2004 | Dunn | | |
| 2004/0083054 A1* | 4/2004 | Jones | G08G 1/123 | |
| | | | 701/465 | |
| 2005/0068169 A1* | 3/2005 | Copley | G08B 21/0283 | |
| | | | 340/539.13 | |
| 2005/0075116 A1* | 4/2005 | Laird | A61B 5/04 | |
| | | | 455/456.3 | |
| 2007/0285260 A1* | 12/2007 | Watanabe | G08B 21/0269 | |
| | | | 340/573.4 | |
| 2008/0068157 A1* | 3/2008 | Ikemori | G08B 21/0222 | |
| | | | 340/539.23 | |
| 2009/0009338 A1* | 1/2009 | Hayashi | G08B 21/0423 | |
| | | | 340/573.1 | |
| 2009/0204434 A1 | 8/2009 | Breazeale, Jr. | | |
| 2010/0225469 A1* | 9/2010 | Yoshioka | G08B 21/0233 | |
| | | | 340/539.13 | |
| 2011/0055546 A1* | 3/2011 | Klassen | G06F 21/305 | |
| | | | 713/150 | |
| 2012/0194388 A1* | 8/2012 | Li | G01S 5/0252 | |
| | | | 342/450 | |
| 2015/0081327 A1 | 3/2015 | Mooker | | |
| 2015/0199896 A1* | 7/2015 | Estes | G08B 27/001 | |
| | | | 340/541 | |
| 2015/0228175 A1* | 8/2015 | Paula-Molina | H04N 7/183 | |
| | | | 348/143 | |
| 2016/0021535 A1* | 1/2016 | Tali | H04W 68/00 | |
| | | | 455/411 | |
| 2016/0071399 A1* | 3/2016 | Altman | H04M 1/72538 | |
| | | | 340/539.11 | |
| 2016/0112835 A1* | 4/2016 | McConathy | H04W 4/021 | |
| | | | 455/456.1 | |
| 2017/0011180 A1 | 1/2017 | Andrews et al. | | |
| 2017/0193306 A1* | 7/2017 | Robil | G06K 9/00771 | |
| 2017/0330459 A1* | 11/2017 | Roach | H04W 4/021 | |
| 2018/0049028 A1* | 2/2018 | Tali | H04W 4/029 | |

OTHER PUBLICATIONS

Episode Solution, LLC, Invitation to Pay Additional Fees and, where applicable, Protest Fee, PCT/US2018/044951, Oct. 29, 2018, 17 pgs.

Episode Solutions, LLC, International Search Report and Written Opinion, PCT/US2018/044951, dated Feb. 8, 2019, 24 pgs.

* cited by examiner

CREATE STEP

STEP NAME
Onboarding

DATE
Diagnosis +24 Hrs

TYPE — 3102
Navigator Patient Call
ROBO Patient Call ← 3104
SMS Message

FORM
United - Joint Onboarding

DESCRIPTION
United - Joint Onboarding

RESOLUTION
Completed

RESOLUTION REQUIRED?
○ Yes

[ CREATE STEP ]   [ CANCEL ]

Figure 31

Patient Ecosystem Platform

Dr. Fitzpatrick

List View | Map View

Location: Surgical Facility
- [ ] Centennial Hospital
- [ ] Baptist Hospital

Radius: 10 Miles ▽

STAR Rating
- [ ] 5 Stars
- [ ] 4 Stars
- [ ] 3 Stars
- [ ] 2 Stars

Avg. Price Per Night
Any  $0 ──────○────── $350+

When Location is Patient Address/Other
Filter By:
○ Distance, Stars, Price
○ Distance, Price, Stars Show: 10 Facilities ▽

Reset | Generate

Preferred SNF   Sort By: Stars ▽

| | Facility | Distance | Stars | Price |
|---|---|---|---|---|
| 1. | NHC @ The Trace | 4.7 Miles | ☆☆ | $650 |
| 2. | Cumberland Health & Rehabilitation Center | 2.9 Miles | ☆☆ | $600 |
| 3. | Bethany Center for Rehabilitation | 1.2 Miles | ☆☆ | $550 |
| 4. | Crestview Health & Rehabilitation | 4.2 Miles | ☆ | $525 |
| 5. | Trevecca Center for Rehabilitation | 3 Miles | ☆ | $500 |

Total: 5

Save

3702
Receive data for a first user including a first identifier associated with the first user

3704
Generate and store the first tracking program for the first user, the first tracking program including the first identifier associated with the first user, a first indicated area for a first user device associated with the first user; and a first time period when the first user is scheduled to be located within the first indicated area

3706
At a first time that corresponds to the first time period, determine, from a position detection system in the first user device, a first determined position of the first user device > 3712
> During the first time period, periodically determine positions of the first user device > 3714
> The first time period includes a designated start time
>
> > 3716
> > The first time that corresponds to the first time period is a predetermined time after the designated start time
>
> > 3718
> > The first time period includes a designated stop time

3720
Compare the first determined position of the first user device with the first indicated area

---
3734
The first tracking program includes a second indicated area for the first user device and a second time period when the first user is scheduled to be located within the second indicated area ---
3736
At a second time that corresponds to the second designated time period, determining, from the position detection system, a second determined position of the first user device ---
3738
Compare the second determined position of the first user device with the second indicated area ---
3740
In accordance with a determination that the second determined position of the first user device does not correspond to the second indicated area, the device transmits a second tracking alert indicating that the first user is not within the second indicated area within the second time period ---
3742
Receive data for a second user including a second device identifier associated with a second user device of a second user ---
3744
Generate and store a second tracking program for the second user

3746
The first tracking program for the first user device includes identifying information for a remote service provider device; and at a second time that corresponds to the first time period, determine, from a position detection system in the remote service provider device, a first determined position of the remote service provider device; compare the first determined position of the remote service provider device with the first indicated area; and, in accordance with a determination that the first determined position of the remote service provider device does not correspond to the first indicated area, transmit a service provider alert indicating that the service provider device is not within the first indicated area within the first time period

---

3748
Determine a set of locations that meet selection criteria, wherein the first indicated area is selected from the set of locations

---

3750
The tracking program includes a first indicated measurement and a measurement time period when the first indicated measurement is to be performed;
at a measurement time that corresponds to the measurement time period, determine whether the first indicated measurement has been performed; and
in accordance with a determination that the first indicated measurement has not been performed, transmit a measurement alert indicating that the first indicated measurement has not been performed

---

3752
At the first time that corresponds to the first time period:
    compare the first determined position of the first user device with an unapproved area; and
    in accordance with a determination that the first determined position of the first user device corresponds to the unapproved area, transmit a second tracking alert indicating that the first user is within the unapproved area within the first time period

3754
The first tracking program includes the unapproved area

| 3802
Receive by an input device, data for a first tracking program for a first user device of a first user, wherein the received data for the first tracking program for the first user device includes a first identifier associated with the first user, a first indicated area for a first user device associated with the first user, and a first time period that corresponds to the first indicated area. |

| 3804
Transmit, to a remote server, the received data for the first tracking program for the first user device |

| 3806
During the first time period, receive, from the remote server, an indication that the first user device is at a second area, distinct from the first indicated area |

| 3808
Display, on the display, a tracking program user interface for the first user device, wherein the tracking program user interface for the first user device includes a second area communication control, that, when activated, initiates communication with a second area communication target |

| 3810
Detect, by the input device, an input at the tracking program user interface |

3812
In accordance with a determination that the input is detected at a position that corresponds to the second area communication control, initiate the communication with the second area communication target

3814
Contact information for the second area communication target is included in the received indication that the first user device is at the second area during the first time period

3816
Initiating the communication with the second area communication target includes automatically generating message text, replacing display of the tracking program user interface with display of a messaging interface that includes a message input field and an address input field, displaying the automatically generated message text in the message input field, and populating the address field with the contact information for the second area communication target

3818
Initiating the communication with the second area communication target includes initiating a telephone call using a phone number included in the contact information for the second area communication target

3820
In response to the receiving the indication that the first user device is at the second area, determine, using locally stored data, contact information for the second area communication target

Figure 38B

TRACKING PROGRAM INTERFACE

RELATED APPLICATIONS

This application is a non-provisional application of and claims priority to U.S. Provisional Patent Application No. 62/540,931, filed Aug. 3, 2017, entitled, "Tracking Program Interface," which is hereby incorporated by reference in its entirety.

TECHNICAL FIELD

This disclosure relates generally to tracking user compliance via location tracking, and more particularly to systems and methods for ensuring that medical patients comply with post-operation programs customized to aid their complete and speedy recovery by tracking and comparing the patients' and their care-givers' locations to predetermined locations like healthcare facilities or the patients' homes.

BACKGROUND

Tracking movement of people is desirable in numerous situations, particularly for users who are required to comply with a predetermined plan that requires the users to be at certain locations at certain times.

For example, a patient who has undergone a medical procedure, such as an orthopedic surgery, may require care in one or more locations after the surgery is complete. Often, following such a medical event, patients fail to seek the necessary follow-up care, which results in costly remedial measures and delayed recovery. For example, patients released from a hospital fail to visit a follow-up facility where the patient is expected, the patient arrives at a different facility where the patient is not expected, or the patient is kept in a facility for a period of time that is longer or shorter than the expected period of time. In such situations, a manager of the patient's care may spend substantial amounts of time locating contact information and contacting various potential facilities, family, or care-givers of the patient. Parties impacted by billing for the medical procedure frequently lack access to information regarding the patient's whereabouts following performance of the medical procedure until long after the post-procedure care is complete. The inability to ensure that a patient complies with follow-up treatment typically leads to costly remedial measures and delayed recovery.

As such, there is a need for care management technology that enables post-event monitoring of users.

SUMMARY

Without limiting the scope of the appended claims, after considering this disclosure, and particularly after considering the section entitled "Detailed Description," one will understand how the aspects of various embodiments are used to determine when a tracked user device is not at an indicated area.

In some embodiments, a method for tracking a user device includes receiving data for a first user including a first identifier associated with the first user. The method also includes generating and storing a first tracking program for the first user. The first tracking program includes the first identifier associated with the first user, a first indicated area for a first user device associated with the first user, and a first time period when the first user is scheduled to be located within the first indicated area. The method also includes, at a first time that corresponds to the first time period, determining, from a position detection system in the first user device, a first determined position of the first user device. The method also includes comparing the first determined position of the first user device with the first indicated area. The method also includes, in accordance with a determination that the first determined position of the first user device does not correspond to the first indicated area, transmitting a first tracking alert indicating that the first user is not within the first indicated area within the first time period.

In some embodiments, a system for tracking a user includes memory, one or more processors, and one or more programs. The one or more programs are stored in the memory and configured to be executed by the one or more processors. The one or more programs include instructions for receiving data for a first user including a first identifier associated with the first user. The one or more programs also include instructions for generating and storing a first tracking program for the first user. The first tracking program includes the first identifier associated with the first user, a first indicated area for a first user device associated with the first user, and a first time period when the first user is scheduled to be located within the first indicated area. The one or more programs also include instructions for, at a first time that corresponds to the first time period, determining, from a position detection system in the first user device, a first determined position of the first user device. The one or more programs also include instructions for comparing the first determined position of the first user device with the first indicated area. The one or more programs also include instructions for, in accordance with a determination that the first determined position of the first user device does not correspond to the first indicated area, transmitting a first tracking alert indicating that the first user is not within the first indicated area within the first time period.

In some embodiments, a computer readable storage medium stores one or more programs. The one or more programs comprise instructions, which when executed, cause a device to receive data for a first user including a first identifier associated with the first user. The one or more programs also include instructions that cause the device to generate and store a first tracking program for the first user. The first tracking program includes the first identifier associated with the first user, a first indicated area for a first user device associated with the first user, and a first time period when the first user is scheduled to be located within the first indicated area. The one or more programs also include instructions that cause the device to, at a first time that corresponds to the first time period, determine, from a position detection system in the first user device, a first determined position of the first user device. The one or more programs also include instructions that cause the device to compare the first determined position of the first user device with the first indicated area. The one or more programs also include instructions that cause the device to, in accordance with a determination that the first determined position of the first user device does not correspond to the first indicated area, transmit a first tracking alert indicating that the first user is not within the first indicated area within the first time period.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features.

FIGS. 5-15 illustrate graphical user interfaces (GUIs) of a tracking management application displayed on a manager device, in accordance with some embodiments.

FIGS. 21-28 illustrate GUIs of tracking management application displayed on a sub-manager device, in accordance with some embodiments.

FIG. 30 illustrates a bundle management interface, in accordance with some embodiments.

FIG. 31 illustrates a step creation user interface, in accordance with some embodiments.

FIG. 33 illustrates a facility selection user interface, in accordance with some embodiments.

FIG. 34 illustrates a tracking program form that includes a drop-down menu that is populated with a list of options that meet selection criteria, in accordance with some embodiments.

FIGS. 37A-37D are flow diagrams illustrating a method for tracking a user device, in accordance with some embodiments.

FIGS. 38A-38D are flow diagrams illustrating a method for communicating with a communication target when a first user device is not at an indicated area, in accordance with some embodiments.

In accordance with common practice, some of the drawings may not depict all of the components of a given system, method or device. Finally, like reference numerals may be used to denote like features throughout the specification and figures.

DETAILED DESCRIPTION

Figure 1:
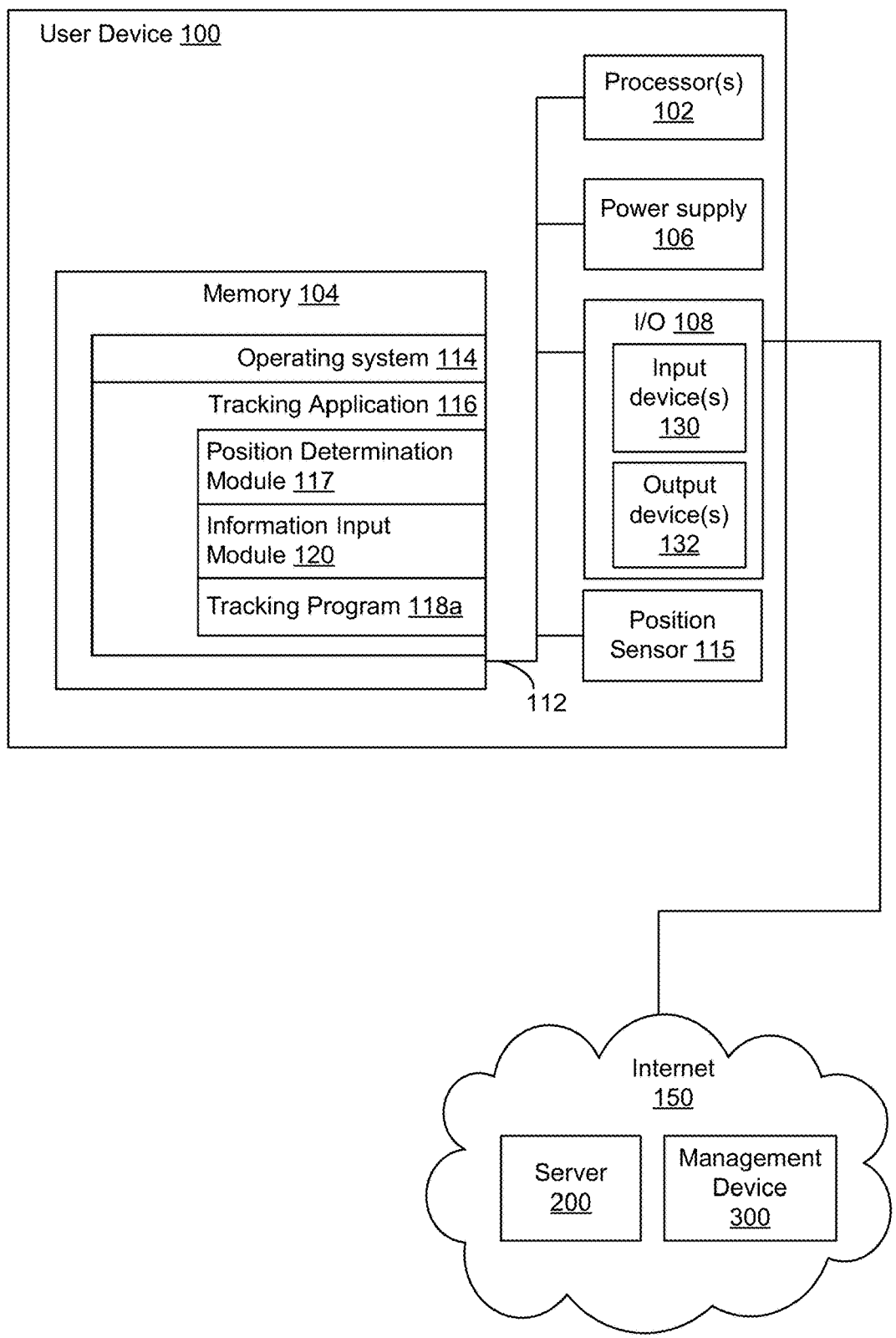
FIG. 1 is a system diagram of a user device, in accordance with some embodiments.

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

The tracking program interface as described herein provides tools for establishing a tracking program for a user and determining whether the user is adhering to or complying with the tracking program. For example, a user is a patient scheduled to undergo a medical procedure. A physician and the patient discuss a proposed plan for patient care that will occur after the medical procedure is complete. The physician or her assistant generates a plan, which is stored as a tracking program that includes information about areas or locations (e.g., a hospital, the user's home, a skilled nursing facility, an inpatient rehabilitation facility, etc.) where the patient will receive care after the procedure, and periods of time that the physician recommends that the patient spend in the indicated areas or locations. Geographical information, such as geofence information, is stored for the areas indicated for patient recovery.

The patient is provided with software to install on their mobile device and/or a dedicated tracking device to monitor patient compliance with the tracking program following the procedure. Thereafter, if the user is determined to be at a location that is not an anticipated or predetermined location of the user, various actions are available to address or remedy the situation. For example, the user may be automatically notified that they are not at the correct location; and/or an alert may be generated at one or more devices accessible by people managing the user's care, such as one or more care managers (e.g., a doctor, such as a surgeon who will perform a medical procedure on the patient) and/or one or more care sub-managers (e.g., another health care practitioner, also referred to herein as a "navigator," such as a nurse, nurse practitioner, and/or physician assistant). On generation of the alert, care managers and/or sub-managers are automatically provided with tools for contacting the user, a contact at area location or facility where the user is present, or a contact at a location or facility where the user was expected to be present.

A tracking system uses geolocation technology to generate automatic responses when a user's movement does not conform to the user's predetermined tracking program. Compared with prior systems that required care managers to contact patients and/or facilities to monitor patient follow-up care, the tracking program interface generates and stores tracking programs, uses location sensing technology to determine adherence to, or compliance with, the tracking programs, and automatically generates tracking alerts so that patients can be brought back on track for a speedy and successful recovery.

Figure 2:
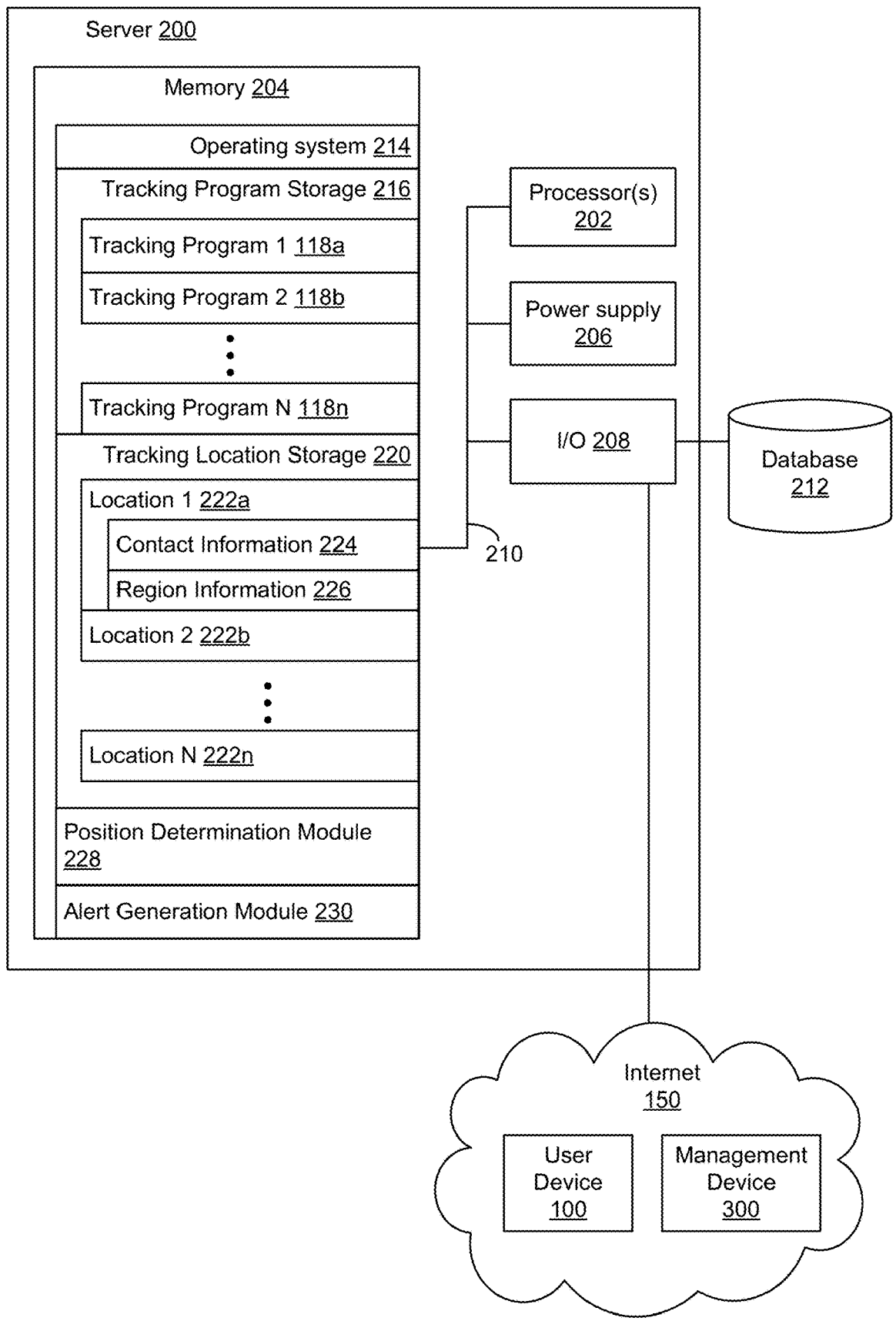
FIG. 2 is a system diagram of a server, in accordance with some embodiments.
Figure 3:
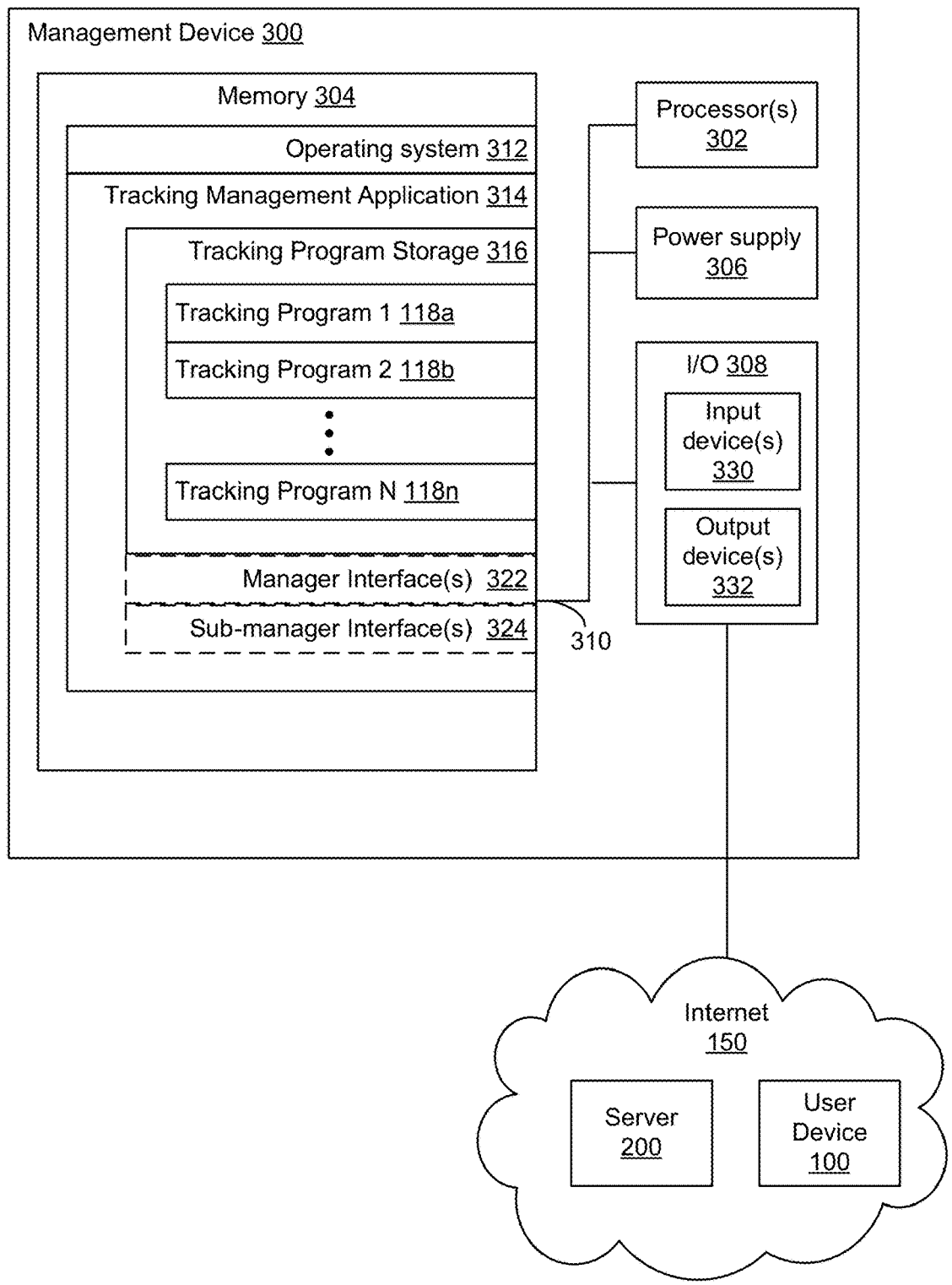
FIG. 3 is a system diagram of a management device, in accordance with some embodiments.

FIGS. 1-3 illustrate devices of a tracking management system. In some embodiments, a tracking management system includes tracking interfaces displayed on a user device (FIG. 1) and/or a management device (FIG. 3). A server (FIG. 2) receives information from and/or transmits information to the user device and/or the management device.

FIG. 1 is a system diagram of user device 100, in accordance with some embodiments. User device 100 typically includes one or more processor(s) 102, a memory 104, a power supply 106, an input/output (I/O) subsystem 108, and a communication bus 112 for interconnecting these components. In some embodiments, user device 100 is a mobile device, such a cellular telephone, tablet, laptop computer and/or a dedicated tracking device. In some embodiments, user device 100 is a device that is carried by an individual receiving care. In some embodiments, user device 100 is a device that is carried by a care provider (e.g., a person scheduled to visit the home of an individual for care following a medical procedure).

Processor(s) 102 execute modules, programs and/or instructions stored in memory 104 and thereby perform processing operations.

In some embodiments, the memory 104 stores one or more programs (e.g., sets of instructions) and/or data structures, collectively referred to as "modules" herein. In some embodiments, memory 104, or the non-transitory computer readable storage medium of memory 104 stores the following programs, modules, and data structures, or a subset or superset thereof:

operating system 114; and tracking application 116, which displays graphical user interfaces and performs operations, for example, as described further with regard to FIGS. 16-20, method 3700 and/or method 3000 below, and including:

position determination module 117, which uses position sensor 115 (e.g., a global positioning system sensor and/or radio frequency antenna) to determine a position of user device 100 (e.g., relative to one or more areas indicated by boundaries such as geofence boundaries);

information input module 112, which prompts a user to input information such as identifying information, health information, and/or contact information (e.g., via user interface 1604 and/or 1704) and/or transmits input user information to server 200; and tracking program 118a, which includes tracking information for the user of user device 100.

The above identified modules (e.g., data structures, and/or programs including sets of instructions) need not be implemented as separate software programs, procedures or modules, and thus various subsets of these modules may be combined or otherwise re-arranged in various embodiments. In some embodiments, memory 104 stores a subset of the modules identified above. Furthermore, the memory 104 may store additional modules not described above. In some embodiments, the modules stored in memory 104, or a non-transitory computer readable storage medium of memory 104, provide instructions for implementing respective operations in the methods described below. In some embodiments, some or all of these modules may be implemented with specialized hardware circuits that subsume part or all of the module functionality. One or more of the above identified elements may be executed by one or more of processor(s) 102. In some embodiments, one or more of the modules described with regard to memory 104 is implemented on memory 204 of server 200 (FIG. 2) and/or memory 304 of management device 300 (FIG. 3).

I/O subsystem 108 communicatively couples user device 100 to local devices (e.g., input device(s) 130 and/or output device(s) 132) and/or remote devices (e.g., devices accessed via a communications network 150 (e.g., the Internet) via a wired and/or wireless connection). For example, in some embodiments, user device 100 is communicatively connected to server 200 and/or management device 300. In some embodiments, a user input device 130 and/or an output device 132 are integrated with device 100 (e.g., a touchscreen display). In some embodiments, user input device 130 and/or an output device 132 are peripheral devices communicatively connected to user device 100. In some embodiments, a user input device 130 includes a keyboard and/or a pointer device such as a mouse, touchpad, touchscreen and/or stylus. In some embodiments, output device 132 includes, e.g., a display and/or a speaker.

Communication bus 112 optionally includes circuitry (sometimes called a chipset) that interconnects and controls communications between system components.

FIG. 2 is a system diagram of server 200, in accordance with some embodiments. Server 200 typically includes one or more processor(s) 202, a memory 204, a power supply 206, an input/output (I/O) subsystem 208, and a communication bus 210 for interconnecting these components.

Processor(s) 202 execute modules, programs and/or instructions stored in memory 204 and thereby perform processing operations.

Figure 4:
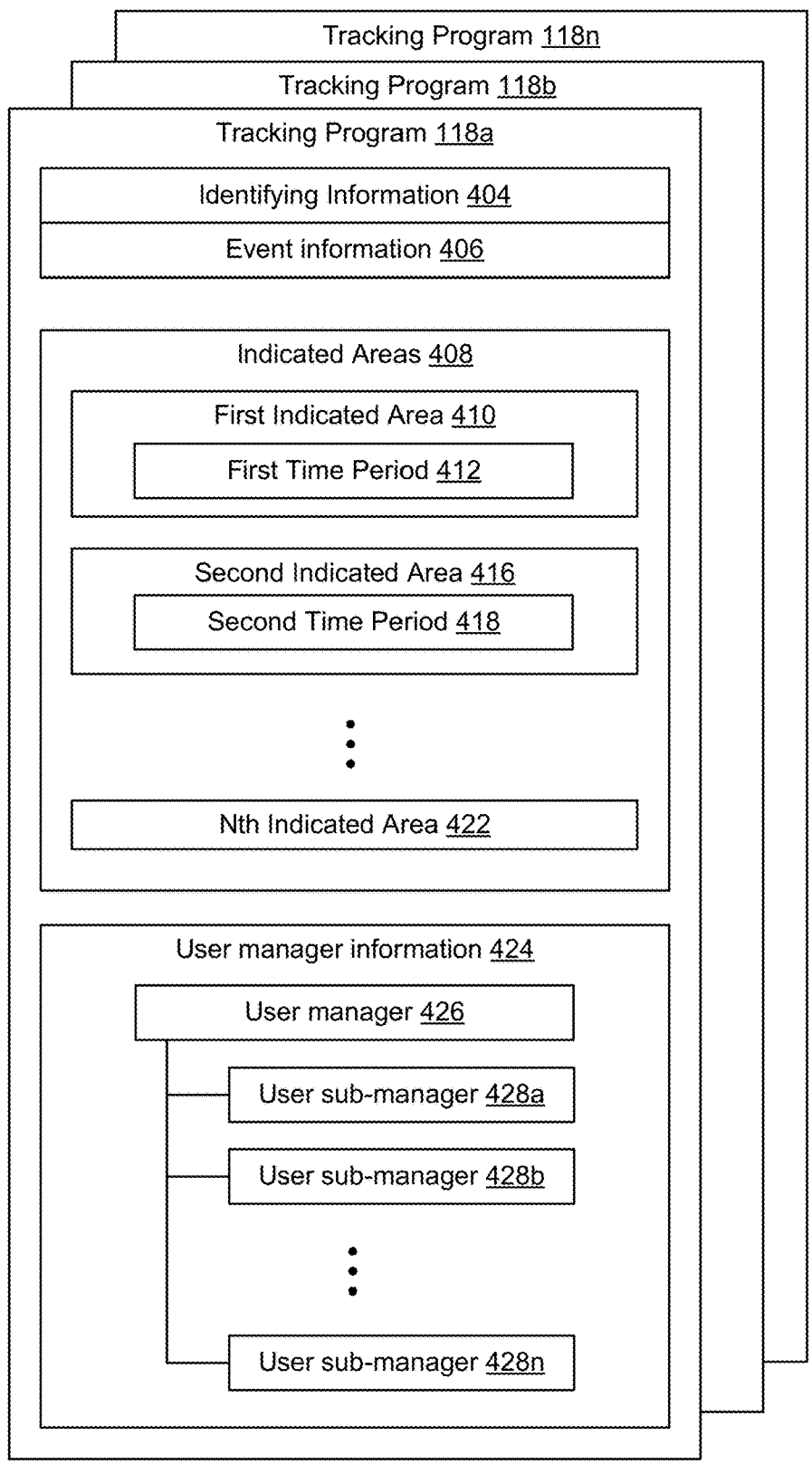
FIG. 4 illustrates an exemplary data structure of a tracking program, in accordance with some embodiments.

In some embodiments, the memory 204 stores one or more programs (e.g., sets of instructions) and/or data structures, collectively referred to as "modules" herein. In some embodiments, memory 204, or the non-transitory computer readable storage medium of memory 204 stores the following programs, modules, and data structures, or a subset or superset thereof:

operating system 214;

tracking program storage 216, which stores one or more tracking programs 118 (e.g., tracking programs 118a, 118b . . . 118n), that have one or more elements of the tracking program data structures 118 as illustrated in FIG. 4;

tracking location storage 220, which stores contact information 224 (e.g., telephone number, e-mail address, network address (e.g., website information), and/or postal address) and/or region information 226 (e.g., geofence data) for one or more care locations 222 (e.g., locations 222a, 222b . . . 222n), such as a user's home, a skilled nursing facility, an inpatient rehabilitation facility, an emergency room, a clinic, a hospital, and/or a physician office;

position determination module 228, which uses position sensor 114 of user device 102 and/or position information received from user device 102 to determine a position of user device 100 (e.g., relative to one or more locations 222); and alert generation module 230, which transmits alert information (e.g., a message (such as an SMS, e-mail, image, audio message, and/or video message), notification, command, user health data, user position data, an indicated area for the user at the current time, and/or contact information for the current user position) to one or more management devices 300.

The above identified modules (e.g., data structures, and/or programs including sets of instructions) need not be implemented as separate software programs, procedures or modules, and thus various subsets of these modules may be combined or otherwise re-arranged in various embodiments. In some embodiments, memory 204 stores a subset of the modules identified above. In some embodiments, database 212 stores one or more modules identified above (e.g., data from tracking programs 118 and/or locations 222). Furthermore, the memory 204 may store additional modules not described above. In some embodiments, the modules stored in memory 204, or a non-transitory computer readable storage medium of memory 204, provide instructions for implementing respective operations in the methods described below. In some embodiments, some or all of these modules may be implemented with specialized hardware circuits that subsume part or all of the module functionality. One or more of the above identified elements may be executed by one or more of processor(s) 202. In some embodiments, one or more of the modules described with regard to memory 204 is implemented on memory 104 of user device 100 (FIG. 1) and/or memory 304 of management device 300 (FIG. 3).

I/O subsystem 208 communicatively couples server 200 to remote devices (e.g., devices accessed via a communications network 150 (e.g., the Internet) via a wired and/or wireless connection). For example, in some embodiments, server 200 is communicatively connected to user device 100 and/or management device 300.

Communication bus 210 optionally includes circuitry (sometimes called a chipset) that interconnects and controls communications between system components.

FIG. 3 is a system diagram of management device 300, in accordance with some embodiments. Management device 300 typically includes one or more processor(s) 302, a memory 304, a power supply 306, an input/output (I/O) subsystem 308, and a communication bus 310 for interconnecting these components. Management device 300 is, for example, a desktop computer or a portable computing device.

Processor(s) 302 execute modules, programs and/or instructions stored in memory 304 and thereby perform processing operations.

In some embodiments, the memory 304 stores one or more programs (e.g., sets of instructions) and/or data structures, collectively referred to as "modules" herein. In some embodiments, memory 304, or the non-transitory computer readable storage medium of memory 304 stores the following programs, modules, and data structures, or a subset or superset thereof:

operating system 312;

tracking management application 314; which displays graphical user interfaces (e.g., manager interface(s) 322 or sub-manager interface(s) 324) and performs operations as described further with regard to FIGS. 5-15, FIGS. 22-28, method 3700 and/or method 3000 below; and tracking program storage 316, which stores one or more tracking programs 118 (e.g., tracking programs 118a, 118b . . . 118n), that have one or more elements of the tracking program data structure 118 illustrated in FIG. 4.

The above identified modules (e.g., data structures, and/or programs including sets of instructions) need not be implemented as separate software programs, procedures or modules, and thus various subsets of these modules may be combined or otherwise re-arranged in various embodiments. In some embodiments, memory 304 stores a subset of the modules identified above. Furthermore, the memory 304 may store additional modules not described above. In some embodiments, the modules stored in memory 304, or a non-transitory computer readable storage medium of memory 304, provide instructions for implementing respective operations in the methods described below. In some embodiments, some or all of these modules may be implemented with specialized hardware circuits that subsume part or all of the module functionality. One or more of the above identified elements may be executed by one or more of processor(s) 302. In some embodiments, one or more of the modules described with regard to memory 304 is implemented on memory 104 of user device 100 (FIG. 1) and/or memory 204 of server 200 (FIG. 2).

I/O subsystem 308 communicatively couples management device 300 to local devices (e.g., input device(s) 330 and/or output device(s) 332) and/or remote devices (e.g., devices accessed via a communications network 150 (e.g., the Internet) via a wired and/or wireless connection). For example, in some embodiments, management device 300 is communicatively connected to user device 100 and/or management device 300. In some embodiments, a user input device 130 and/or an output device 132 are integrated with device 100 (e.g., a touchscreen display). In some embodiments, user input device 330 and/or an output device 332 are peripheral devices communicatively connected to management device 300. In some embodiments, a user input device 330 includes a keyboard and/or a pointer device such as a mouse, touchpad, touchscreen and/or stylus. In some embodiments, output device 332 includes, e.g., a display and/or a speaker.

Communication bus 310 optionally includes circuitry (sometimes called a chipset) that interconnects and controls communications between system components.

FIG. 4 illustrates an exemplary data structure of a tracking program 118, in accordance with some embodiments. A tracking program is, for example, a document or other data file, and/or a set of data stored in a database, that stores identifying information 404 (e.g., for a user and/or for a device) and/or one or more indicated areas 408 (e.g., first indicated area 410, second indicated area 416 . . . Nth indicated area 422) indicated for the user and/or user device. In some embodiments, identifying information 404 includes user identifying information such as name, date of birth, and/or a unique identifier such as a Medicare ID and/or electronic medical record number. In some embodiments, identifying information 404 includes device identifying information such as telephone number and/or a unique identifier for the device such as a device serial number. In some embodiments, a first indicated area is a region (e.g., a region that corresponds to a home and/or a healthcare facility) indicated by a boundary, such as a geofence. In some embodiments, a first indicated area is a city, zip code, address, and/or set of geographic coordinates. A first time period 412 is indicated for first indicated area 410, a second time period 418 is indicated for second indicated area 418, and so on. In some embodiments, one or more indicated areas 408 (e.g., 410, 416 . . . 422) correspond to locations 222 (e.g., 222a, 222b, . . . 222c) as described with regard to FIG. 2 (e.g., geographical information for a location 222 is stored as an indicated area 408). When a manager user interface 322 is used to indicate an area 408, a location 222 that corresponds to the area 408 is stored by the server 200 and/or a link (e.g., a database relationship) is created between an indicated area 408 and a location 222.

In some embodiments, the user provides identifying information 404 for tracking program 118 via a user interface of a tracking application 116 (e.g., a user interface generated by information input module 120 for display by an output device 132 of user device 100). In some embodiments, tracking application 116 automatically transmits identifying information to server 200. In some embodiments, tracking program 118 includes event information 406 (e.g., a name of a surgical procedure to be performed). For example, for a user that has a scheduled event (e.g., a surgery), a user manager (e.g., a surgeon) can provide input via a user interface of a tracking management application 314 (e.g., a user interface generated by a tracking management application 314 for display by an output device 332 of management device 300) to indicate one or more areas where the patient will receive care following the event, and periods of time where the patient will receive care at each location. identifying information 404

In some embodiments, tracking program 118 includes information (e.g., identifying information and/or contact information) for one or more care managers 426 (e.g., a doctor, such as a surgeon who will perform a medical procedure on the patient) and/or one or more care sub-managers 409 (409a, 409b, . . . 409n), (e.g., another health care practitioner, also referred to herein as a "navigator," such as a nurse, nurse practitioner, physician assistant, and/or a caregiver who visits the patient after a medical procedure is complete).

In some embodiments, tracking program 118 includes information about an item (e.g., an area, facility, provider, procedure, and/or device) that is unapproved for the patient (e.g., not covered by the patient's insurance, does not meet a required quality rating, and/or beyond a threshold distance from a location associated with the tracking program). In some embodiments, a time period is stored in association with an unapproved location. In some embodiments, an indicated area is stored in association with an unapproved location. In this way, the tracking program 118 is usable to generate an alert when a patient has arrived at an unapproved location.

In some embodiments, tracking program 118 includes information about devices to be used by the patient and/or measurements to be performed by the patient. For example, a device to be used by a patient is a blood pressure monitor, heart rate monitor, blood analysis device, or scale. In some embodiments, the device is configured to communicate with user device 100 (e.g., via a wired and/or wireless communication connection). In some embodiments, the plan indicates times at which devices are to be used and/or measurements are to be performed. In this way, tracking program 118 is usable to generate an alert when a patient has not performed an indicated measurement.

In some embodiments, user input provided via a user interface (e.g., a respective user interface of user interfaces 5-28 and 30-35) is stored in one or more of identifying information 404, event information 406, indicated areas 408, indicated time periods (412, 418) user manager information 424, unapproved areas, devices, and/or measurements. In some embodiments, one or more of identifying information 404, event information 406, indicated areas 408, indicated time periods (412, 418) user manager information 424, unapproved areas, devices, and/or measurements is automatically generated (e.g., based on pre-determined values and/or previously created tracking programs).

FIGS. 5-15 illustrate graphical user interfaces (GUIs) (e.g., manager interfaces 322) of tracking management application 314, in accordance with some embodiments. For example, the GUIs of FIGS. 5-15 are displayed on output device 332 (e.g., a display) of management device 300.

Figure 5:
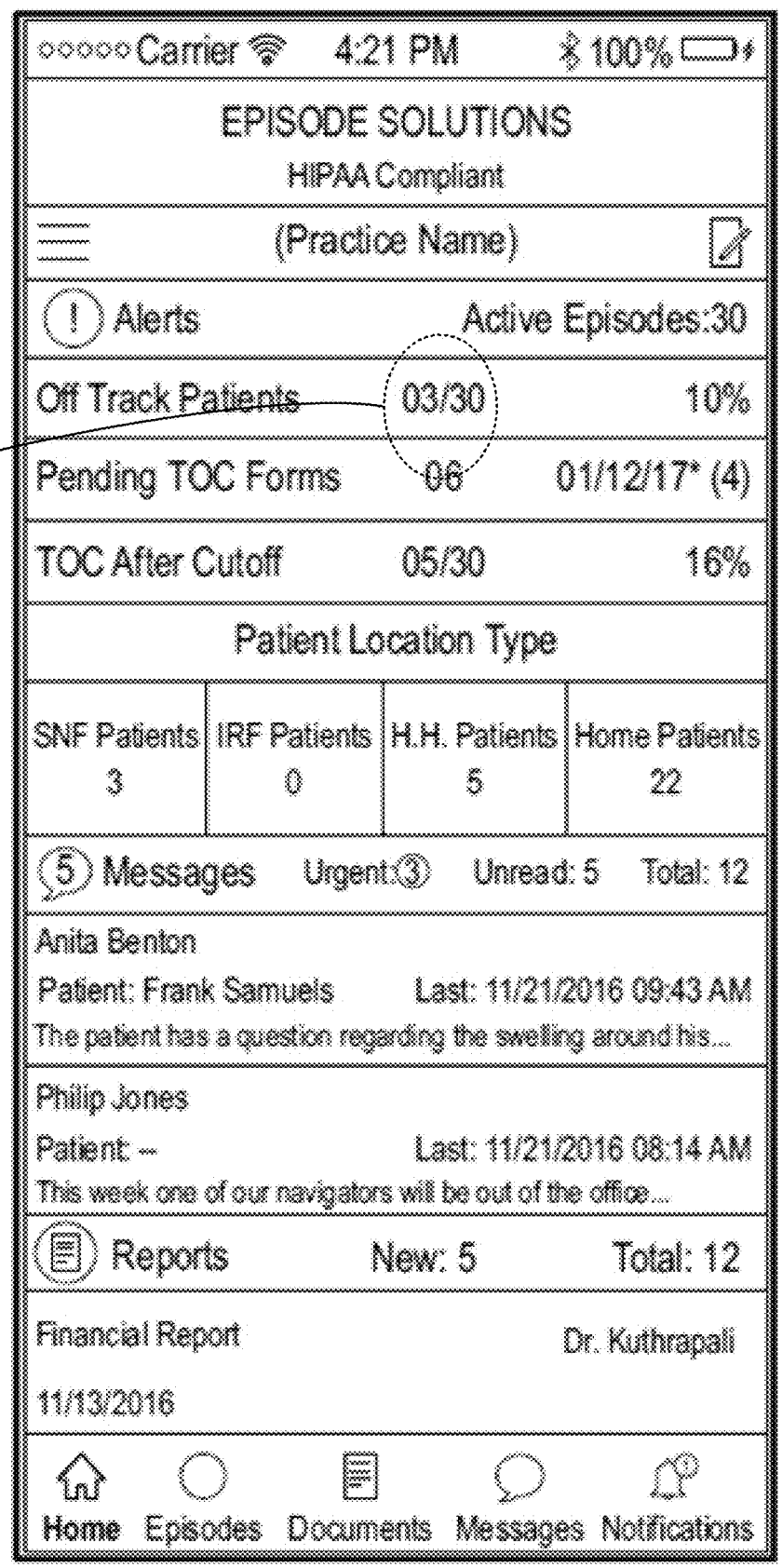
Figure 6:
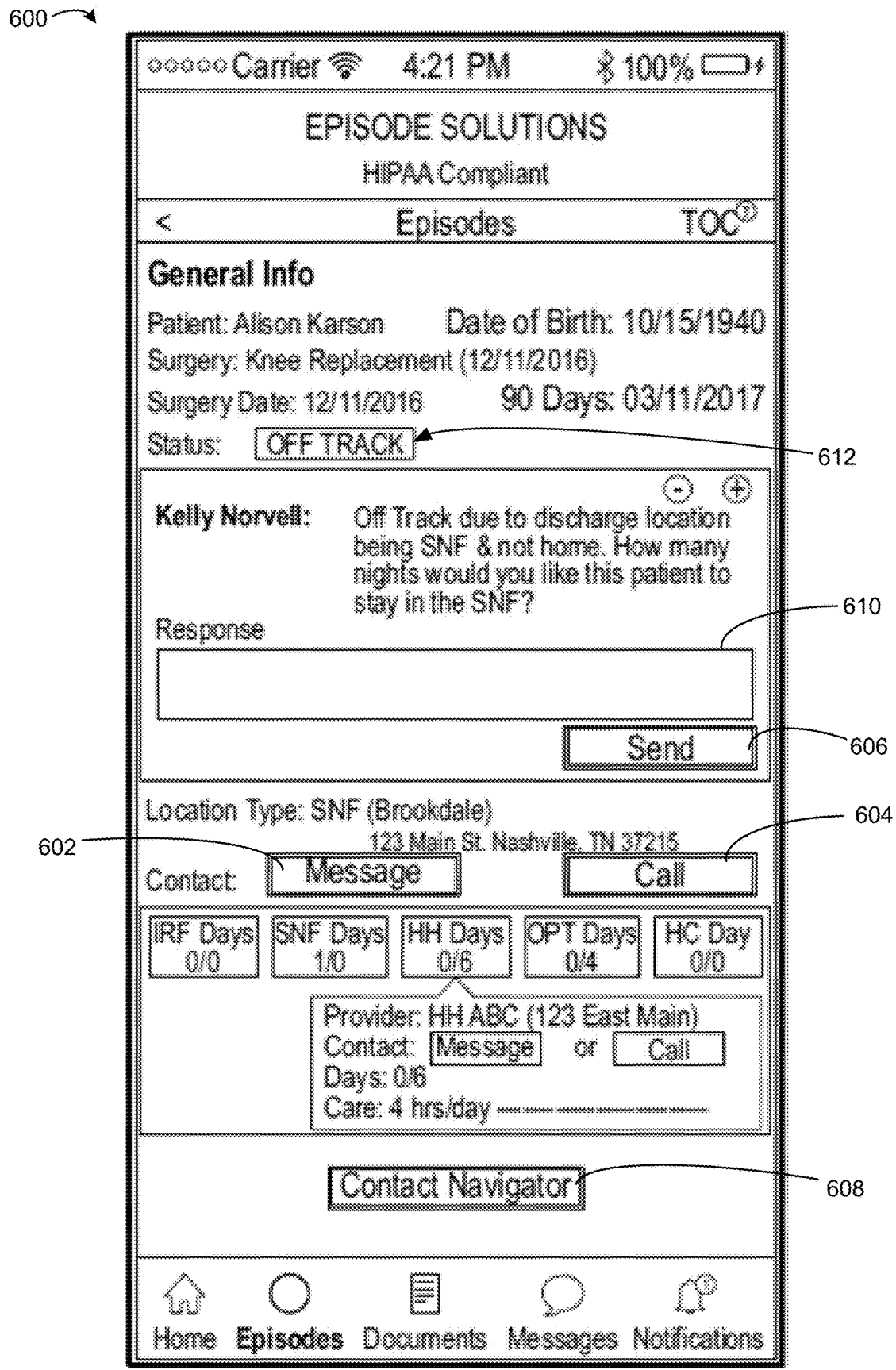

In FIG. 5, a manager user interface home page 500 is displayed on management device 300. In some embodiments, in response to an input (e.g., a contact with a touchscreen display) at a location that corresponds to displayed alert data for off-track patients, as indicated at 504, an episode user interface, such as user interface 600 (FIG. 6) user interface 1200c (FIG. 12) is displayed.

Figure 7:
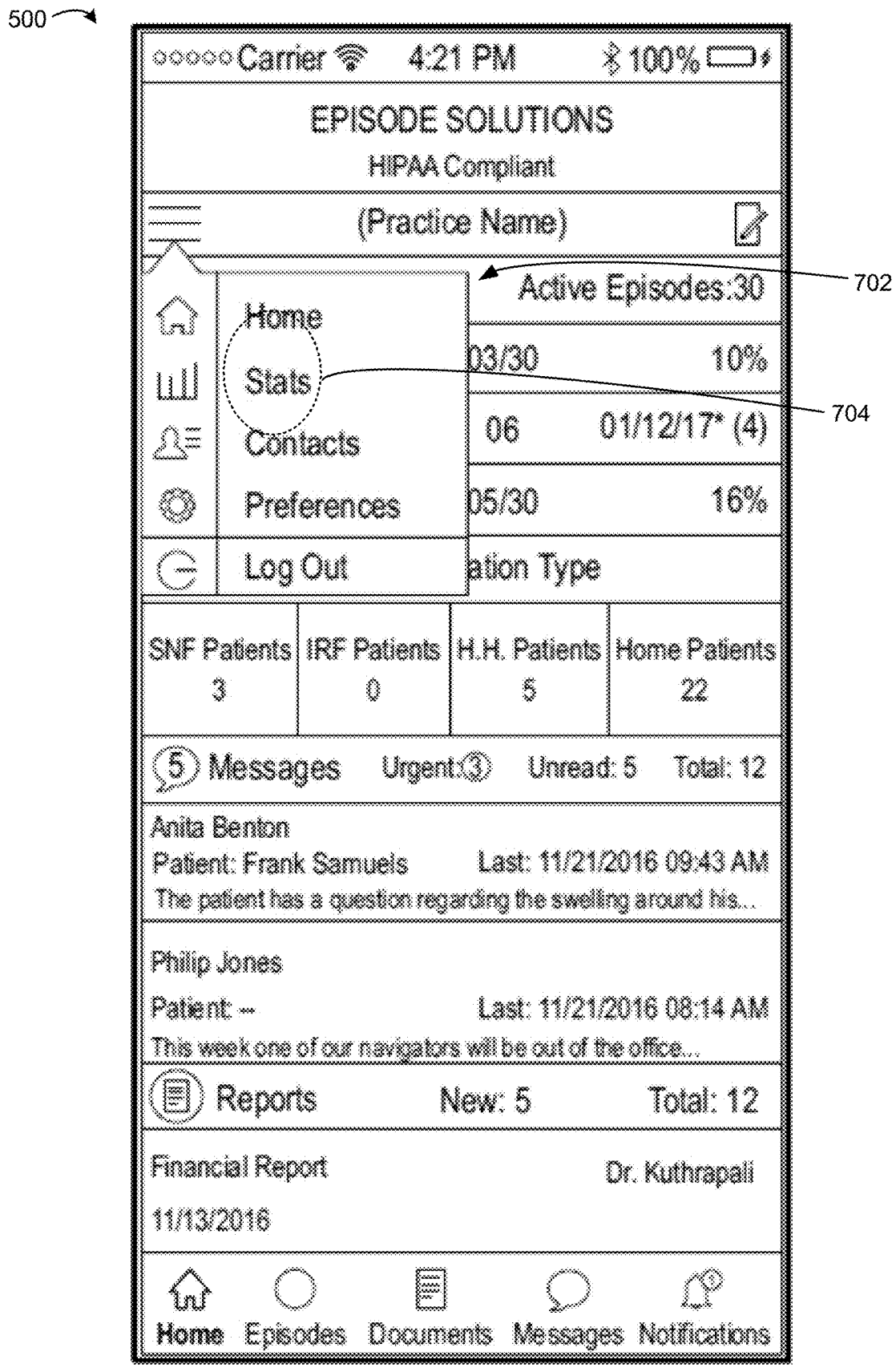
Figure 8:
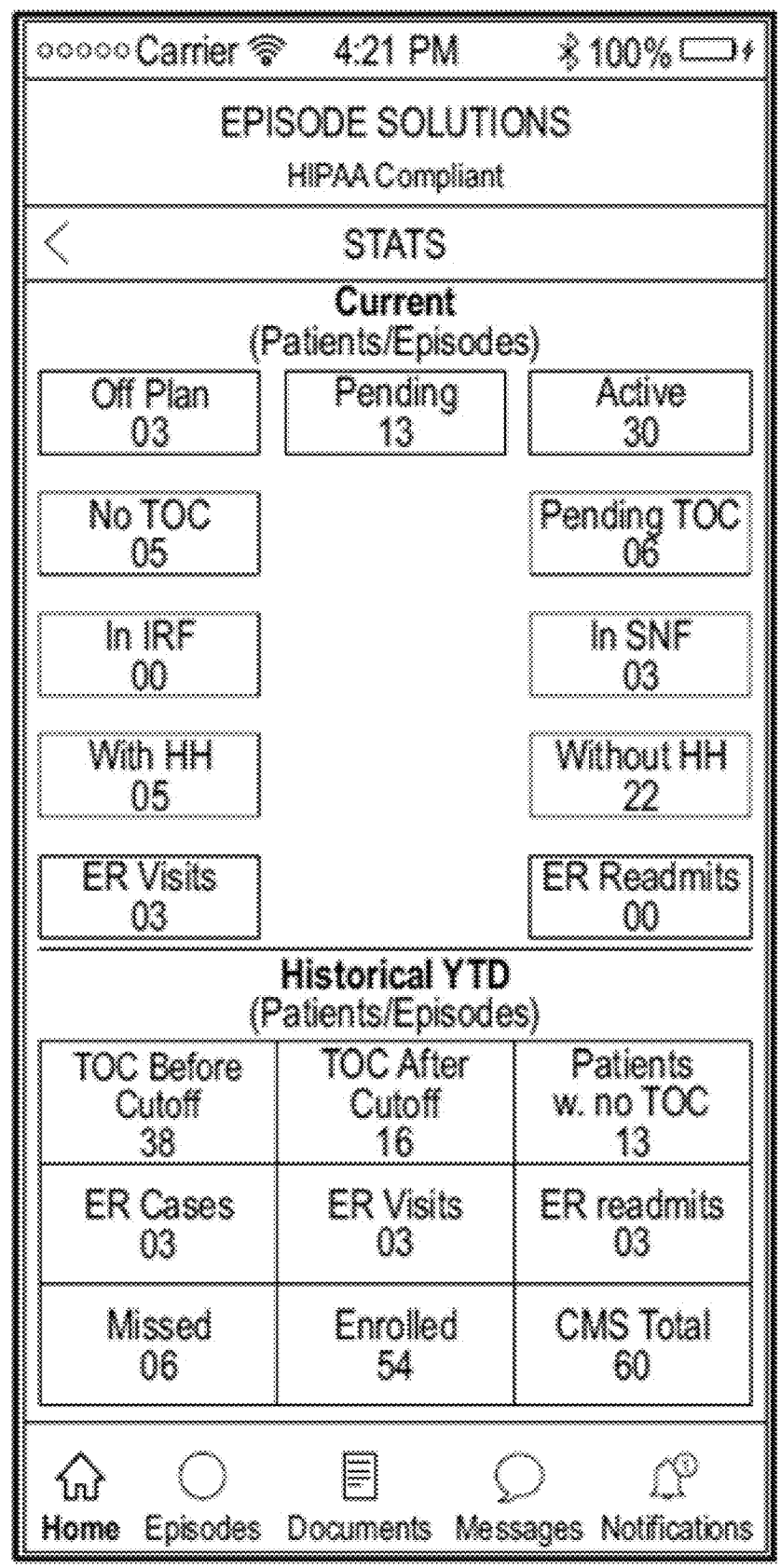
Figure 9:

In FIG. 7, a drop-down menu 702 is displayed overlaying manager user interface home page 500. In response to an input detected while user interface 600 is displayed (e.g., at a location that corresponds to the "Stats" menu item of drop-down menu 702, as indicated at 704, statistical information user interface 800 is displayed, as shown in FIG. 8. In response to an input detected at a location that corresponds to the "Preferences" menu item of drop-down menu 702, contact preferences user interface 900 is displayed, as shown in FIG. 9.

Statistical information user interface 800 includes information about current user device positions for multiple user devices 100. For example, in the illustrative example of FIG. 8, the user interface displays information indicating that zero user devices are located in inpatient rehabilitation facilities (IRF), three user devices are located in in skilled nursing facilities (SNF), five user devices are located at a user's home as the user receives home healthcare (HH), and three user devices are located at (or have been located at, following a procedure) an emergency room (ER). Statistical information user interface 800 additionally displays information about tracking programs 118 (e.g., transition of care (TOC) plans) that are missing. For example, a number displayed in a region entitled "No TOC" indicates a number of patients that are scheduled for surgery but for whom no TOC has been generated, and a number displayed in a region entitled "Pending TOC" indicates a number of TOCs that have been generated and that require review and sign-off. A number displayed in a region entitled "Off plan" indicates a number of user devices with determined locations that are different from indicated areas during a corresponding indicated time frame (and/or user devices with determined locations that correspond to unapproved areas). A number displayed in a region entitled "Pending" indicates a number of users scheduled for a procedure that have not yet undergone the procedure, and a number displayed in a region entitled "Active" indicates a number of users for whom tracking programs are active (e.g., an event is occurring and/or a current time is during an indicated time period).

Preferences user interface 900 allows a manager to input identifying information and/or preference information, such as a preferred communication mode, preferred contact information (e.g., for a given mode), and/or alert parameter preferences.

Figure 10:
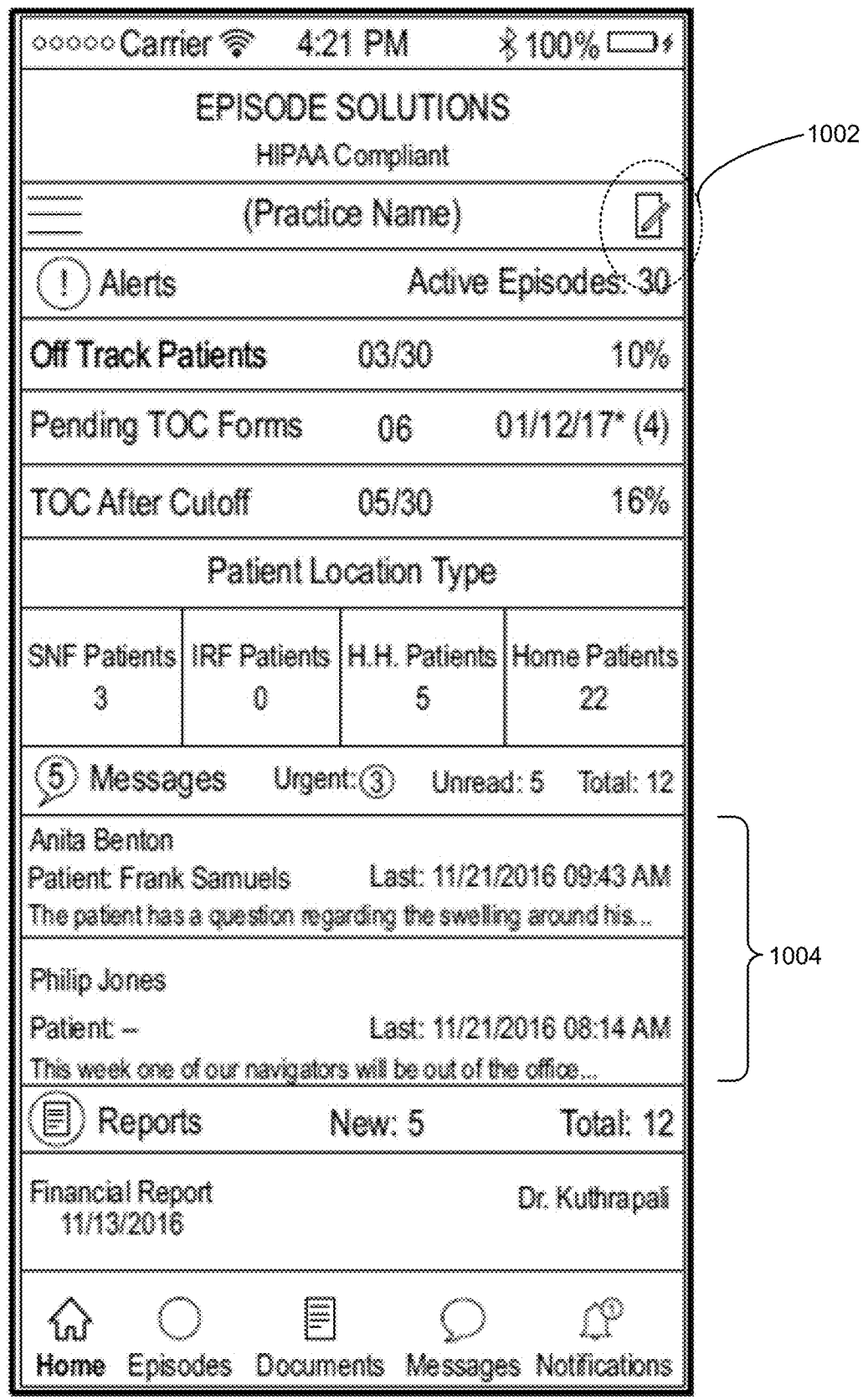
Figure 11:
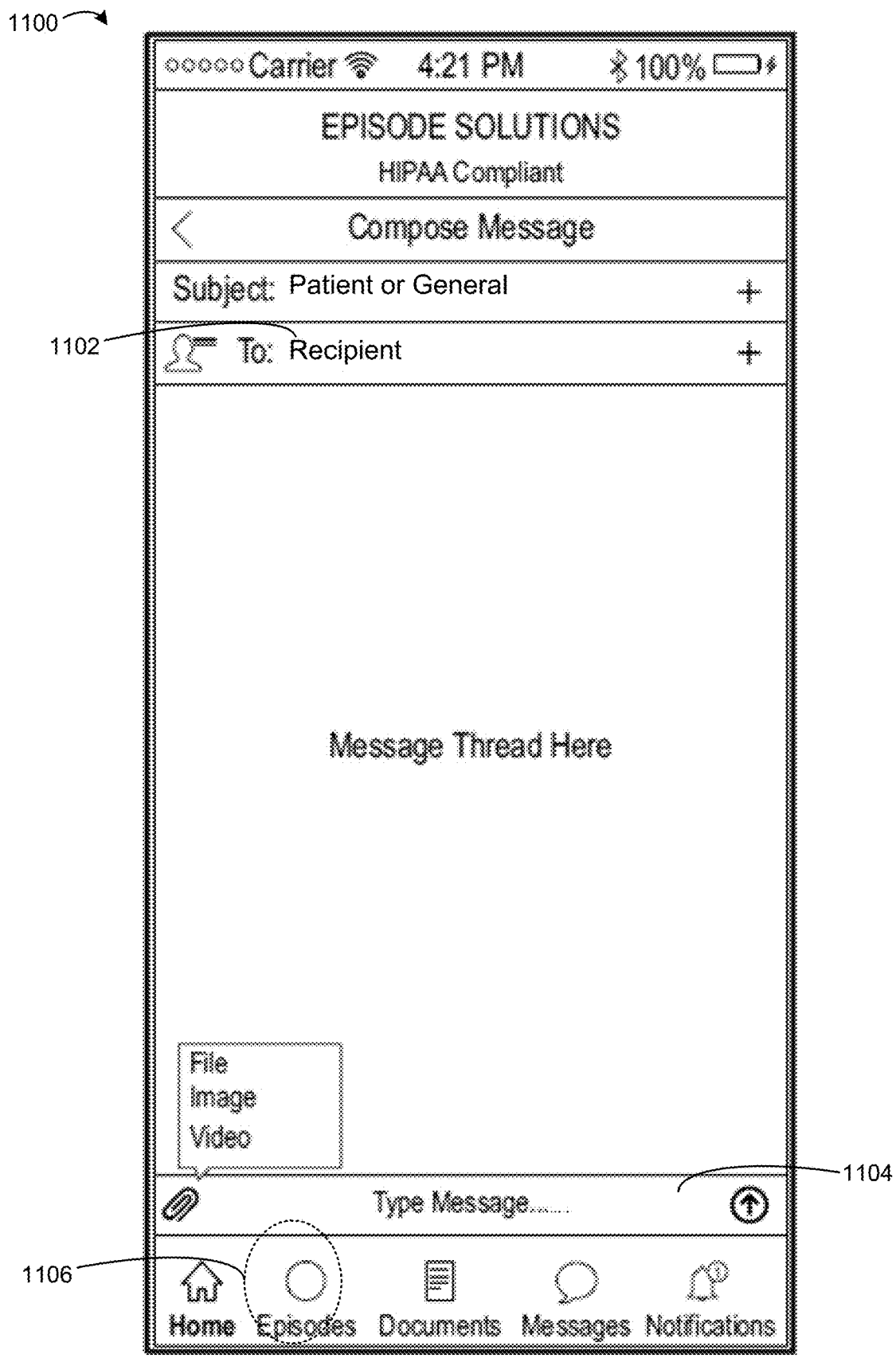

In FIG. 10, manager user interface home page 500 is displayed, and an input is detected at a location indicated at 1002. In response to the input, messaging information user interface 1100 is displayed, as shown in FIG. 11. In some embodiments, one or more messages that correspond to tracking alerts (e.g., received by management device 300 from server 200) are displayed in a priority position within a messaging section 1004 of manager user interface home page 500 and/or within a messaging user interface. For example, one or more messages that correspond to tracking alerts are displayed at the top of a list of messages. In some embodiments, an order of displayed message information in a list of messages is dependent on an off-track parameter, such as a length of time that a patient that is the subject of a respective message has been off track.

Figure 12:
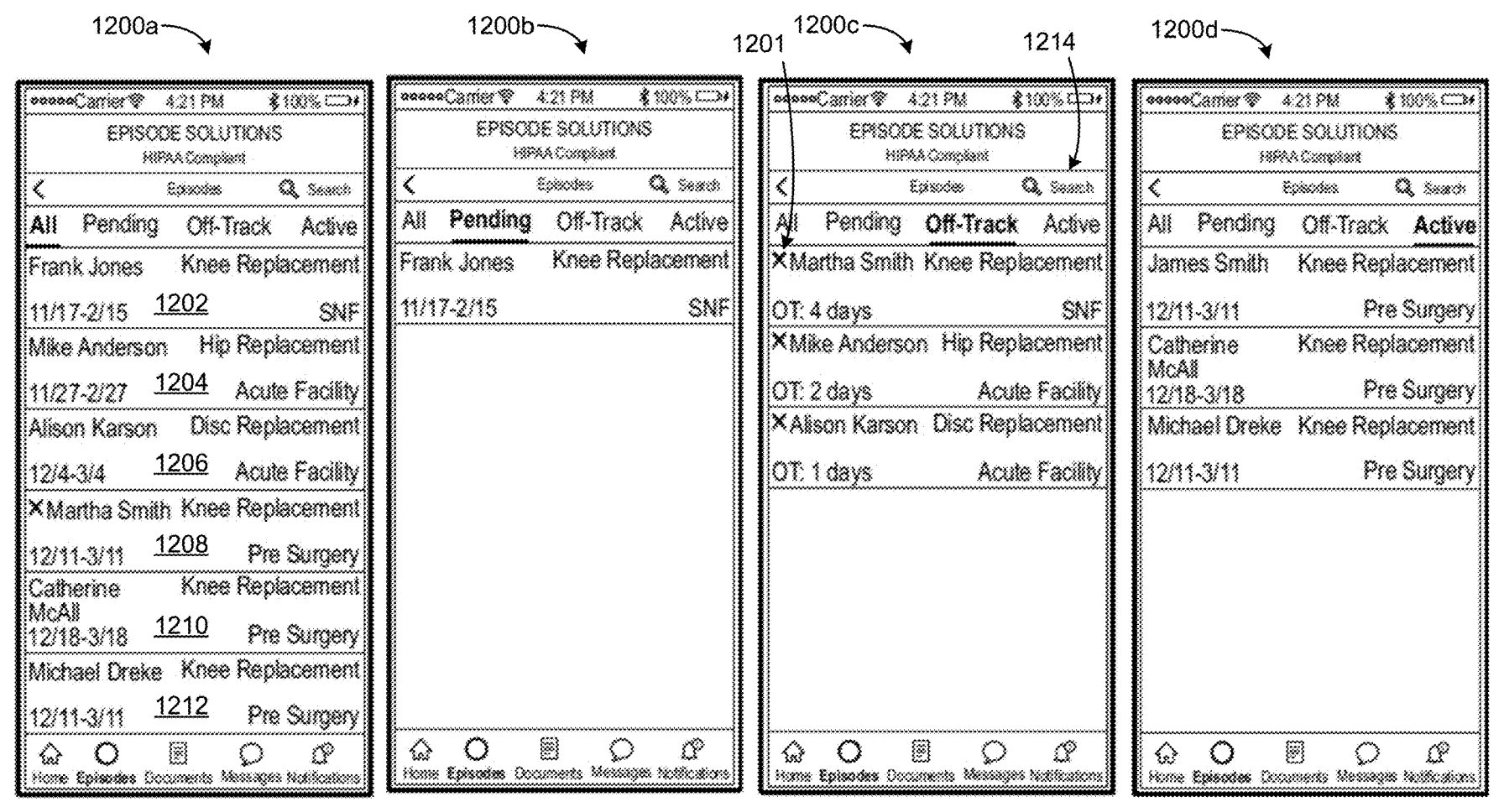

In FIG. 11, an input is detected at a location corresponding to an episode display control, as indicated at 1106. In response to the input, a default and/or most recently displayed state of episode interface 1200 (e.g., 1200a, 1200b, 1200c, 1200d) is displayed, as shown in FIG. 12. 1200a, 1200b, 1200c, 1200d illustrate filters (all, pending, off-track, active) applied to a set of episode records (1202-1212). A search control 1214, when selected, allows a user to filter the set of tracking program items using a search input. In some embodiments, when a tracking alert has been received for a user device, a visual indicator (e.g., a background coloration, text coloration, text effect, animation, and/or marker), such as alert marker 1201, is applied to episode record (e.g., adjacent to information for the user device). In some embodiments, a list of off-track episode records is ordered in accordance with an off-track parameter such as a length of time (e.g., number of days) that a user device has been off track. For example, a user device of "Martha Smith" in 1200c has been off-track for 4 days (e.g., as indicated by the text "OT: 4 days"). Because the user device of Martha Smith has been off track for a longer period of time (4 days) than Mike Anderson (2 days), the episode record for "Martha Smith" is shown before the episode record for Mike Anderson in the list of episode records.

In response to an input at a location that corresponds to an episode record (e.g., an input at a location that corresponds to one of episode records 1202-1212 as shown in FIG.

Figure 13:
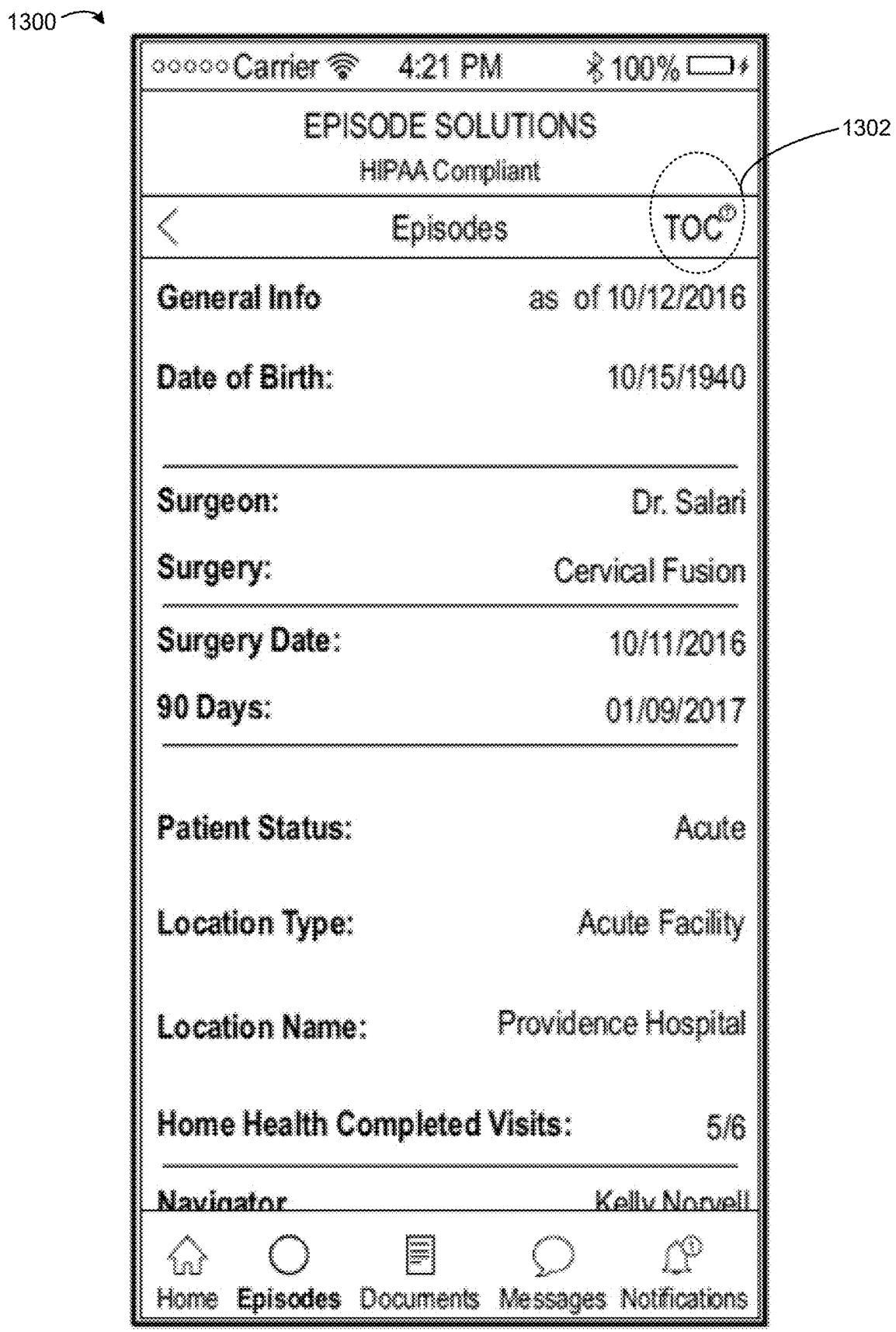

1200*a*, or one of the episode records shown in 1200*b*, 1200*c*, or 1200*d*) a tracking program item interface 1300 is displayed, as shown in FIG. 13. In response to an input at a location that corresponds to a tracking program display control, as indicated at 1302, a tracking program form (TOC form) 1400 is displayed, as shown in FIG. 14.

Figure 14:
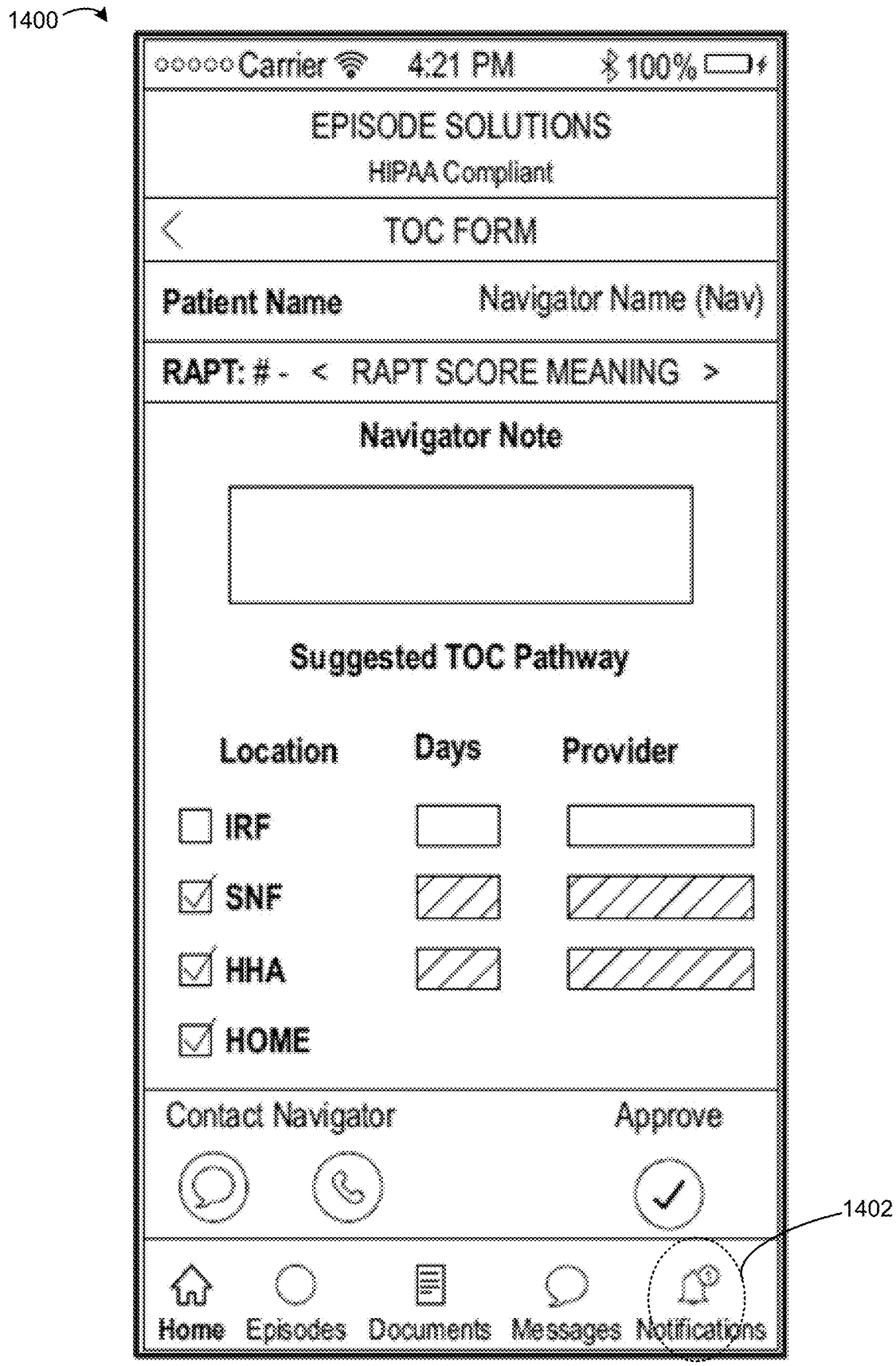

FIG. 14 shows an interface that is used by a manager device 300 to generate identifying information 404 (e.g., via input provided in the "Patient Name" field), a first indicated area 410, a first time period 412, a second indicated area 416, and/or a second time period 418 (e.g., via information provided in one or more fields and/or checkboxes of the "Suggested TOC Pathway") for a tracking program 404 (e.g., a TOC). For example, a physician checks a box for SNF, enters a number of days (e.g., a number of days following a medical procedure or a number of days following a period of time indicated for a previous indicated area) in the "Days" field that corresponds to the SNF checkbox, and indicates a particular indicated area in the "Provider" field that corresponds to the SNF checkbox. In some embodiments, an indicated area is selected from a list (e.g., a list populated with items that meet selection criteria), as discussed further with regard to FIG. 35.

Figure 15:
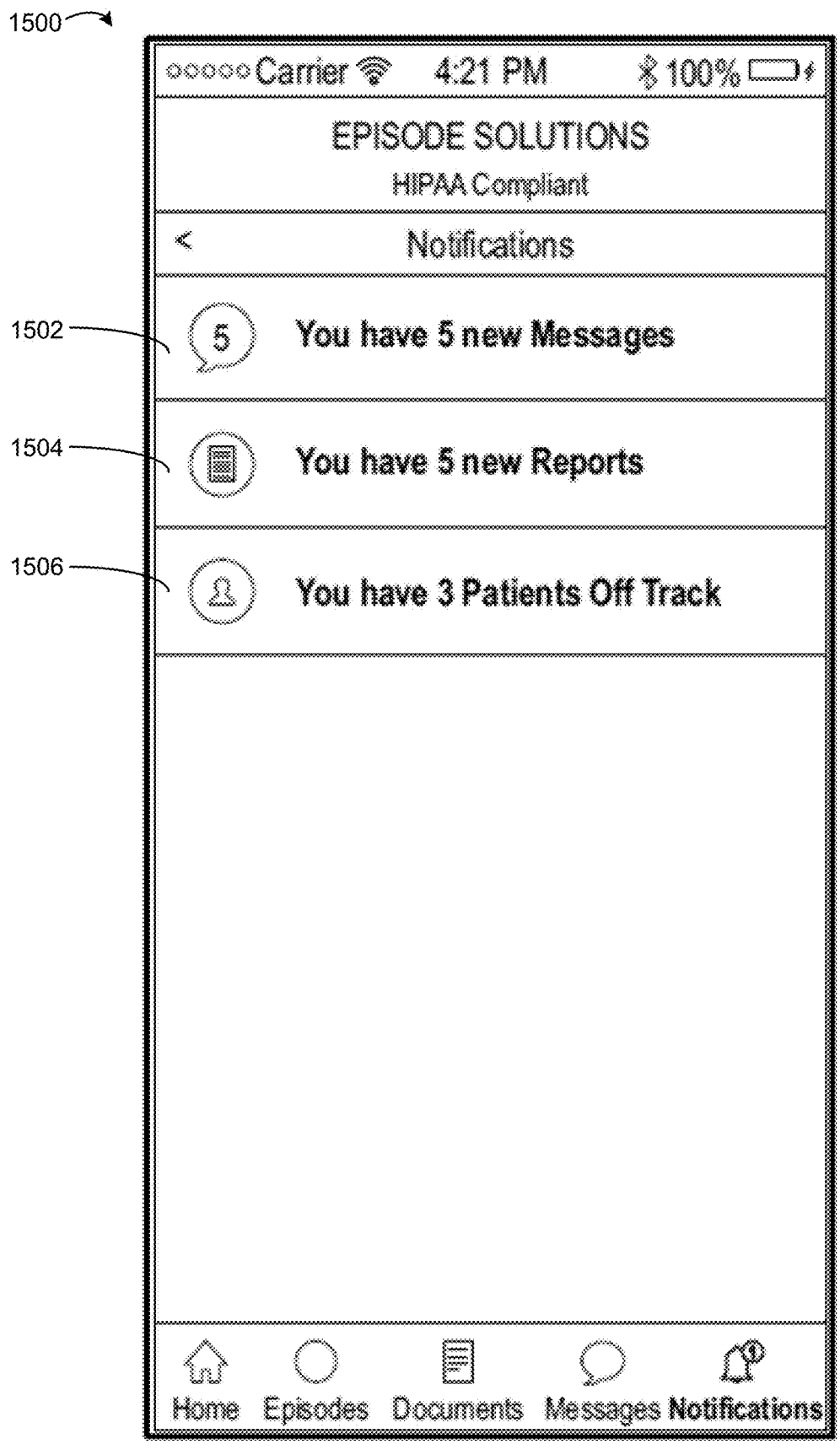
Figure 16:
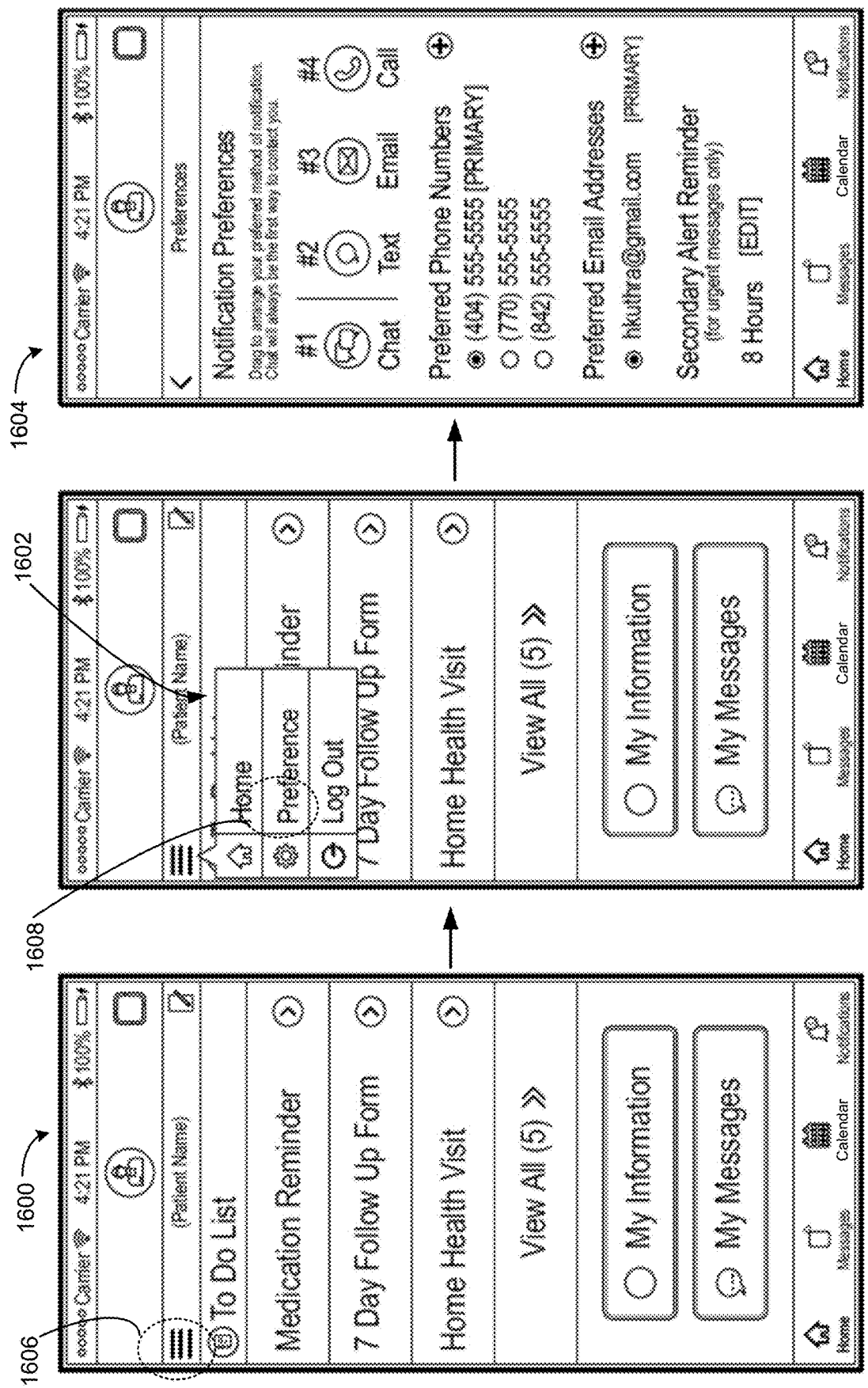
FIGS. 16-20 illustrate GUIs of a tracking application on a user device, in accordance with some embodiments.

In response to an input at a location that corresponds to a notification user interface display control, as indicated at 1402, a notification interface 1500 is displayed, as shown in FIG. 15. The notification interface indicates, for example, a number of new messages (as indicated at 1502), a number of new reports requiring review and/or approval (as indicated at 1504), and a number of patients of track (as indicated at 1506).

FIGS. 16-20 illustrate GUIs of user tracking application 116, in accordance with some embodiments. For example, the GUIs of FIGS. 16-20 are displayed on output device 132 (e.g., a display) of user device 100.

While a user portal home page 1600 of user tracking application 116 is displayed, an input is detected at a location that corresponds to a menu display control, as indicated at 1606. In response to the input, a menu 1602 is displayed overlaying home user interface 1600. In response to an input at a location that corresponds to a "Preference" menu item, as indicated at 1608, a contact preference user interface 1604 is displayed. In some embodiments, a user of user device 100 provides input using contact preference user interface 1604 to generate identifying information 404. For example, identifying information 404 is transmitted from user device 100 to server 200 and/or management device 300.

Figure 17:
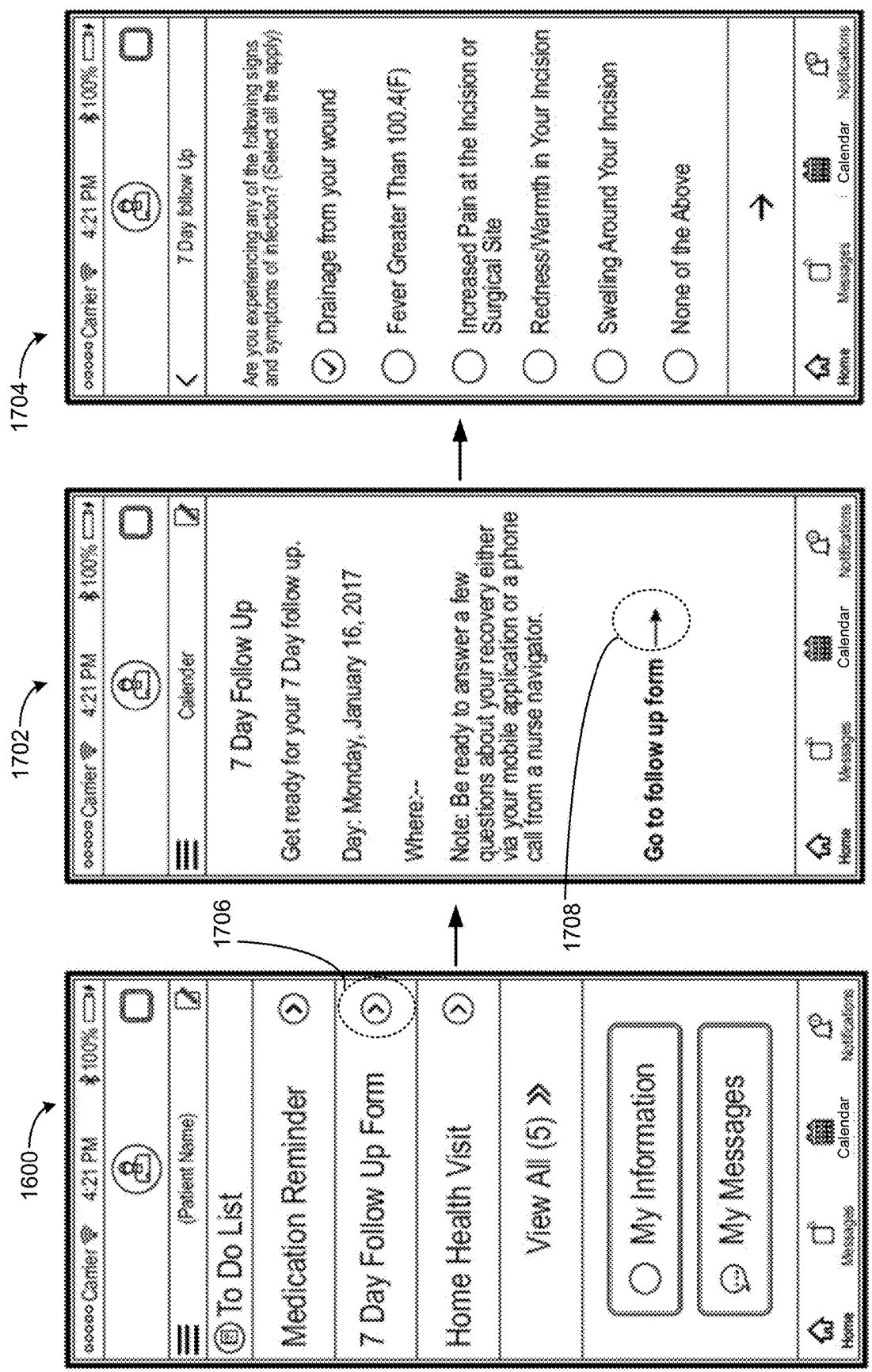

In FIG. 17, while home user interface 1600 of user tracking application 116 is displayed, an input is detected at a location that corresponds to a "7 Day Follow Up Form" item in a to-do list, as indicated at 1706. In response to the input, a "7 Day Follow Up Form" note page 1702 is displayed. In response to an input at a location that corresponds to a "Go to follow up form" control, as indicated at 1708, a follow up survey user interface 1704 sheet is displayed.

Figure 18:
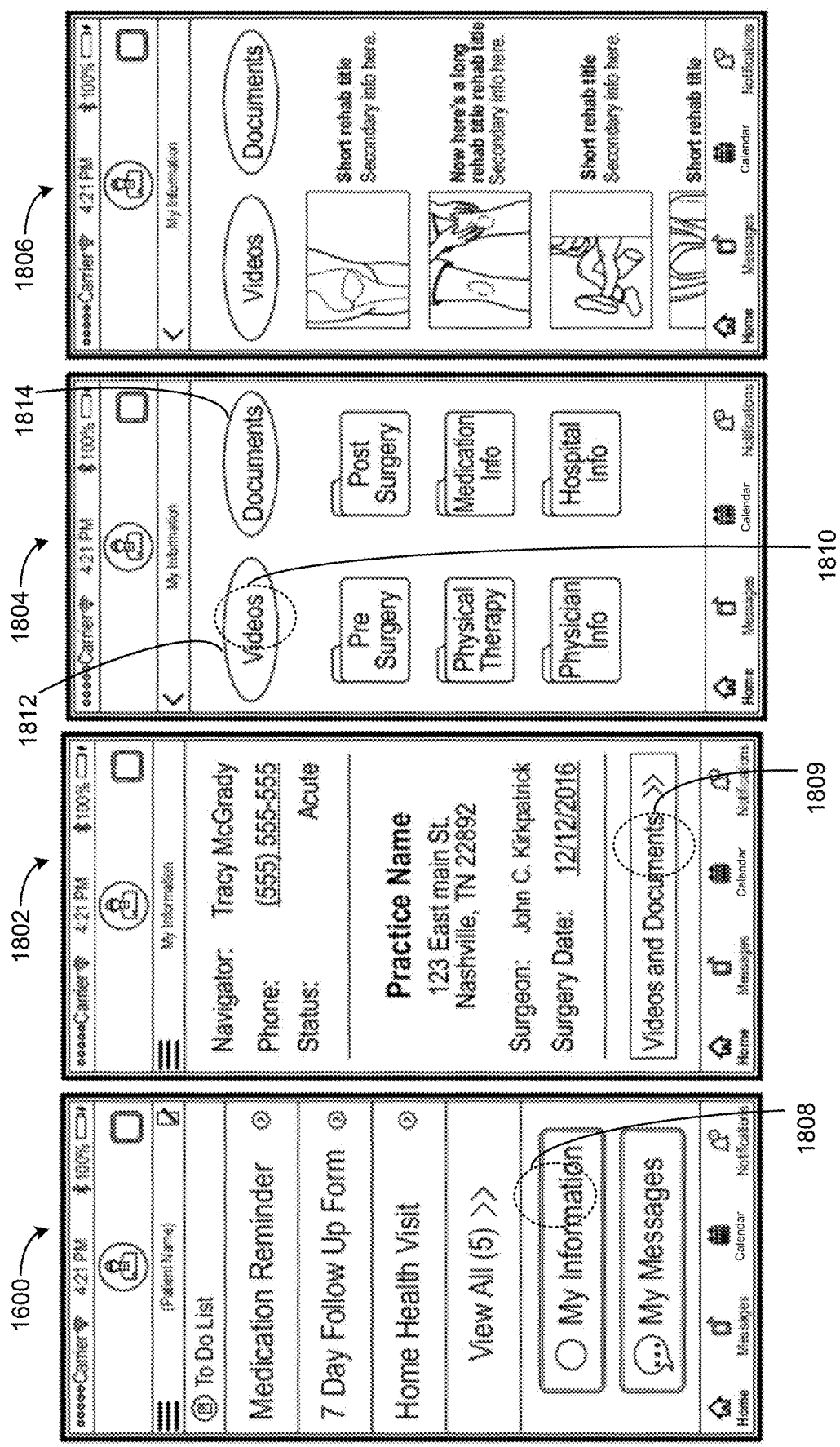

FIG. 18 illustrates input 1808 at user portal home page 1600 to display an information page 1802. In response to input 1809 detected at a "Videos and Documents" control, a document page 1804 is displayed and/or a videos page 1806 is displayed. Videos control 1812 and documents control 1814, when activated, cause a corresponding document to be displayed. Input 1810 detected at a location that corresponds to video control, as shown in 1804, causes a documents page 1804 to be displayed. Documents page 1804 and/or videos page 1806 provide information to the patient, for example, about a medical procedure and/or information that is useful to the patient following the procedure.

Figure 19:
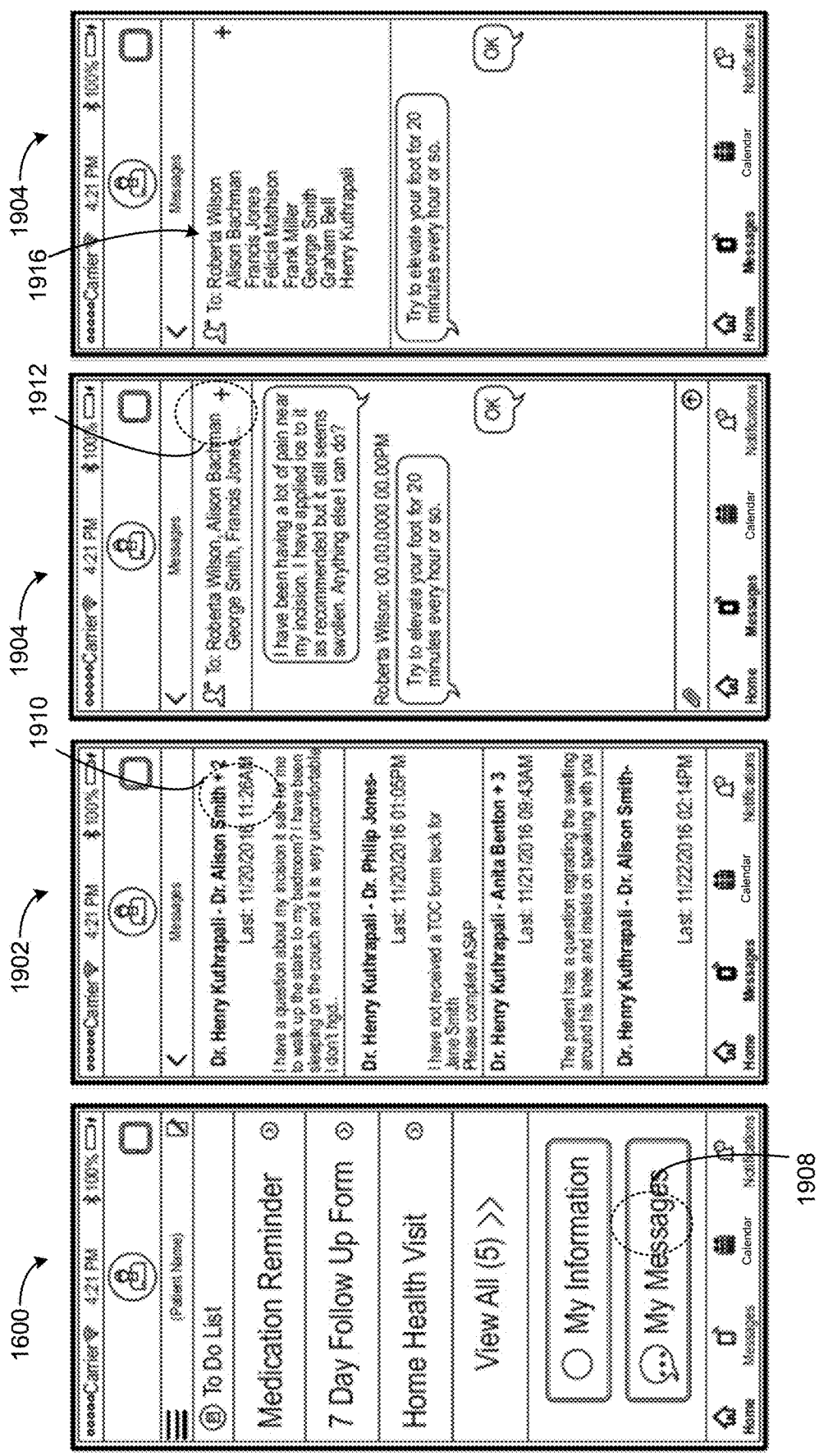

FIG. 19 illustrates input 1908 at user portal home page 1600 to display a messages user interface 1902. In response to input 1910 detected at a message record display in messages interface 1902, a message transcript user interface 1904 is displayed. In response to input 1912 detected at a contact list control displayed in message transcript user interface 1904, a list of contacts 1916 is displayed (e.g., overlayed over message transcript user interface 1904). In some embodiments, the list of contacts is auto-populated with one or more user managers 426 and/or user sub-managers 428 stored in a tracking program 118.

Figure 20:
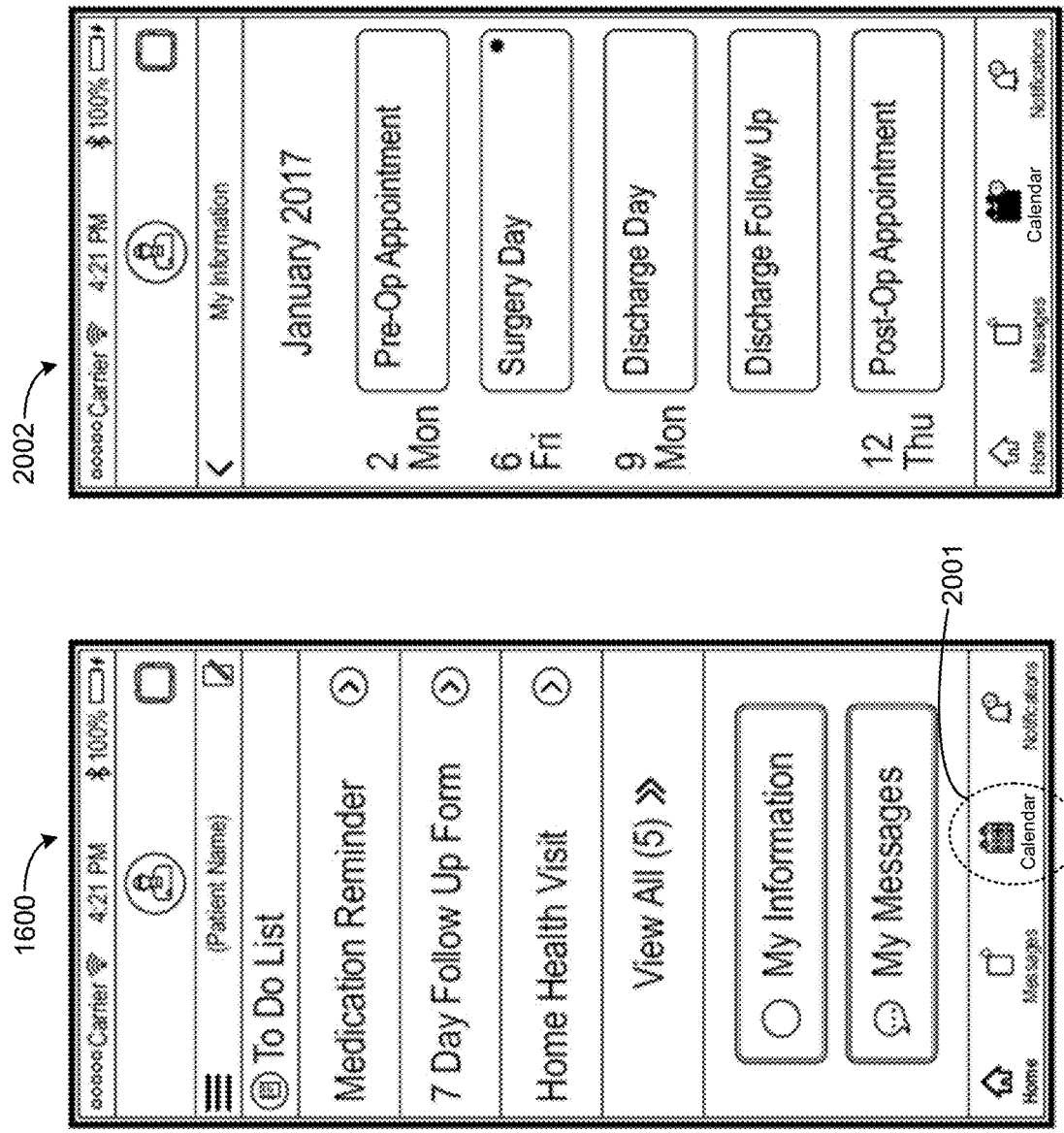

FIG. 20 illustrates input 2001 received at user portal home page 1600 to display a calendar interface 2002. In some embodiments, the calendar displayed in calendar interface 2002 is populated with tracking program information received by user device 100 from server 200, such as event information 406, first indicated area 410, first time period 412, second indicated area 416, and/or second time period 418.

FIGS. 21-28 illustrate GUIs (e.g., sub-manager interfaces 324) of tracking management application 314, in accordance with some embodiments. For example, the GUIs of FIGS. 21-28 are displayed on output device 332 (e.g., a display) of management device 300.

Figure 21:
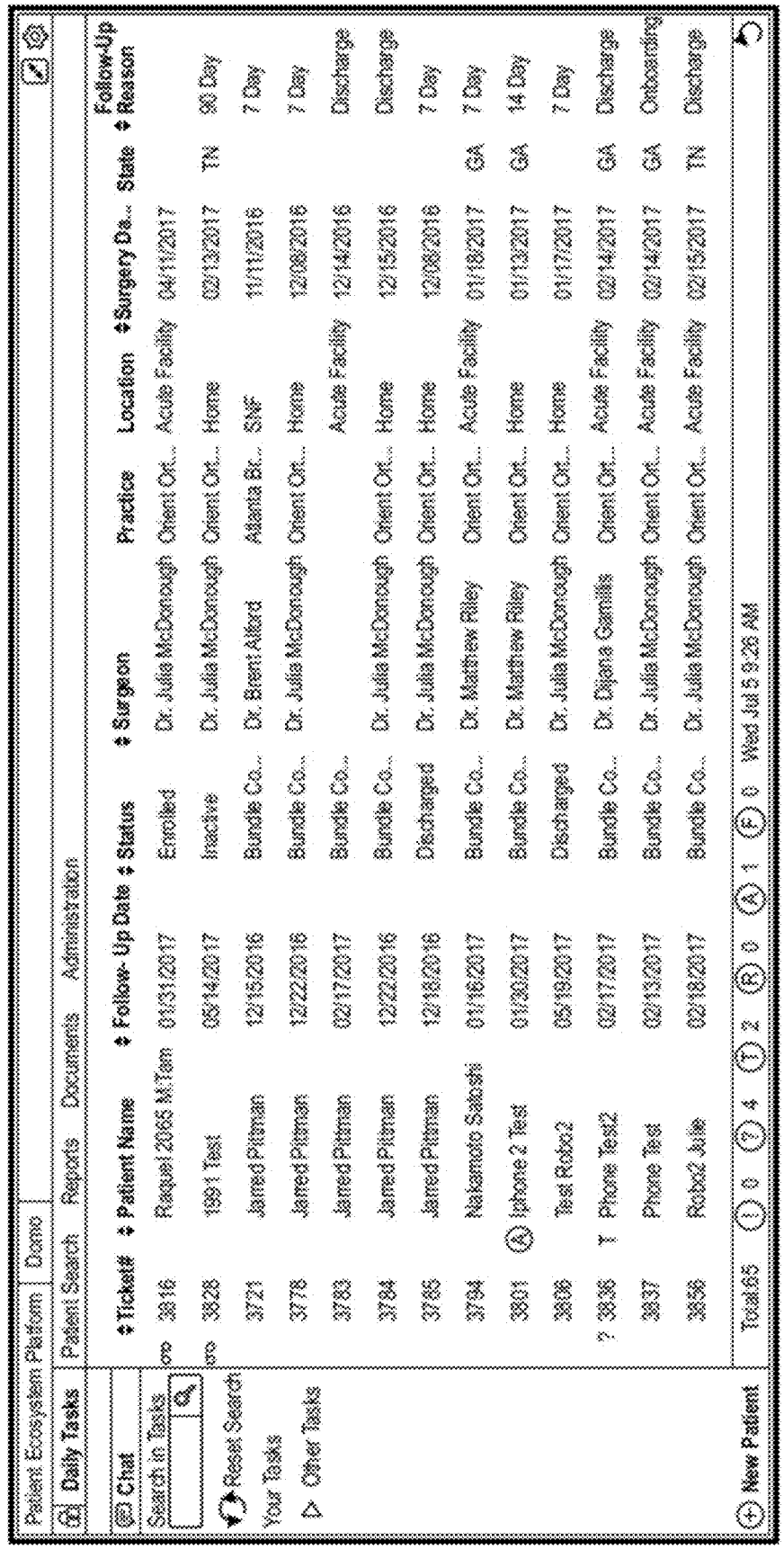

In FIG. 21, a sub-manager task user interface 2100 is displayed on management device 300. The sub-manager task user interface 2100 displays a plurality of tasks for a sub-manager generated, for example, based on tracking programs 118 for a plurality of users. In some embodiments, tracking alert information is displayed at a location that corresponds to one or more patients in the sub-manager task user interface 2100. For example, in response to a tracking alert (e.g., received by management device 300 from server 200), a visual indicator (e.g., a background coloration, text coloration, text effect, animation, and/or marker) is applied to a patient record (e.g., adjacent to identifying information for the user).

Figure 22:
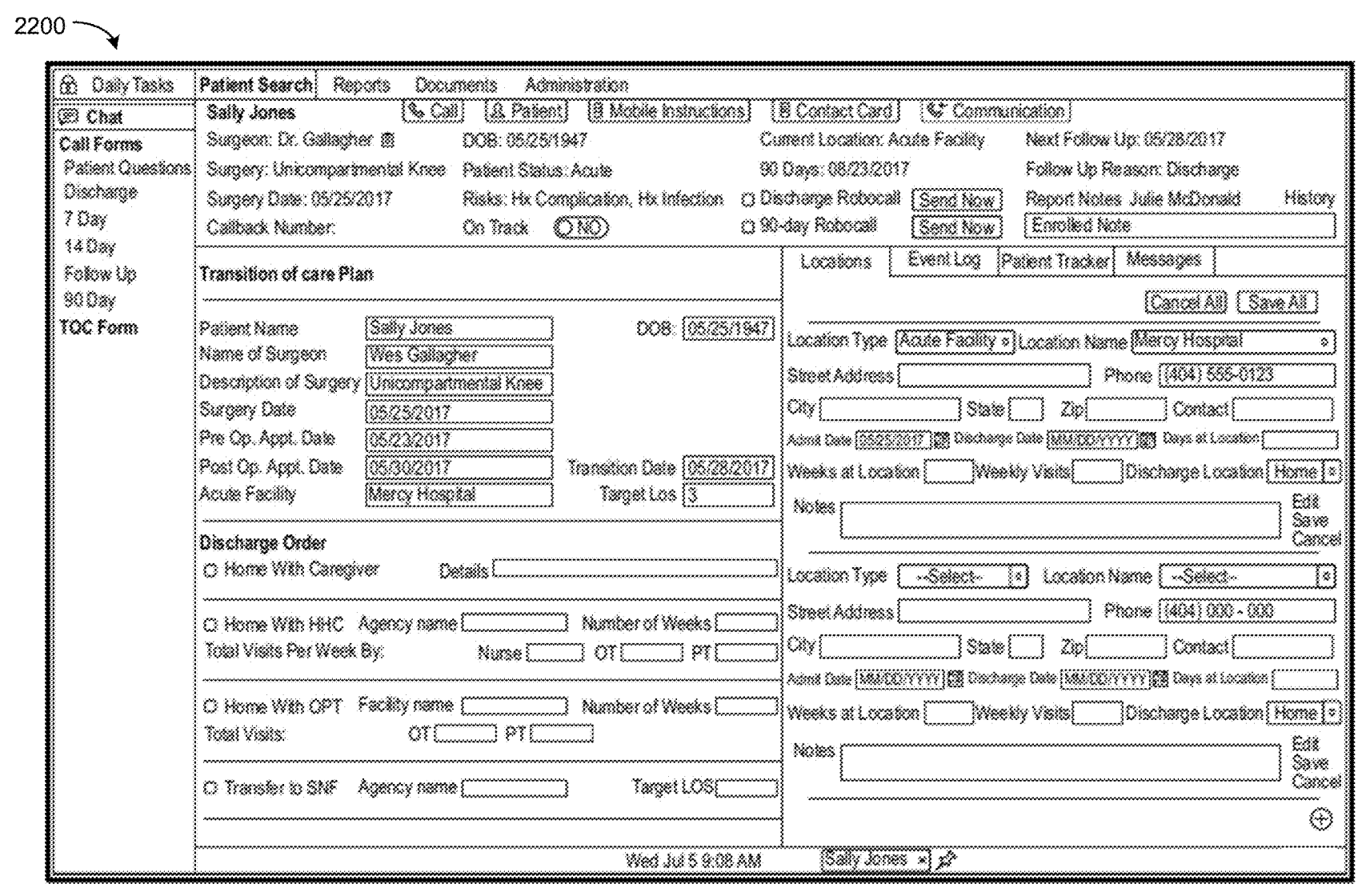
Figure 23:
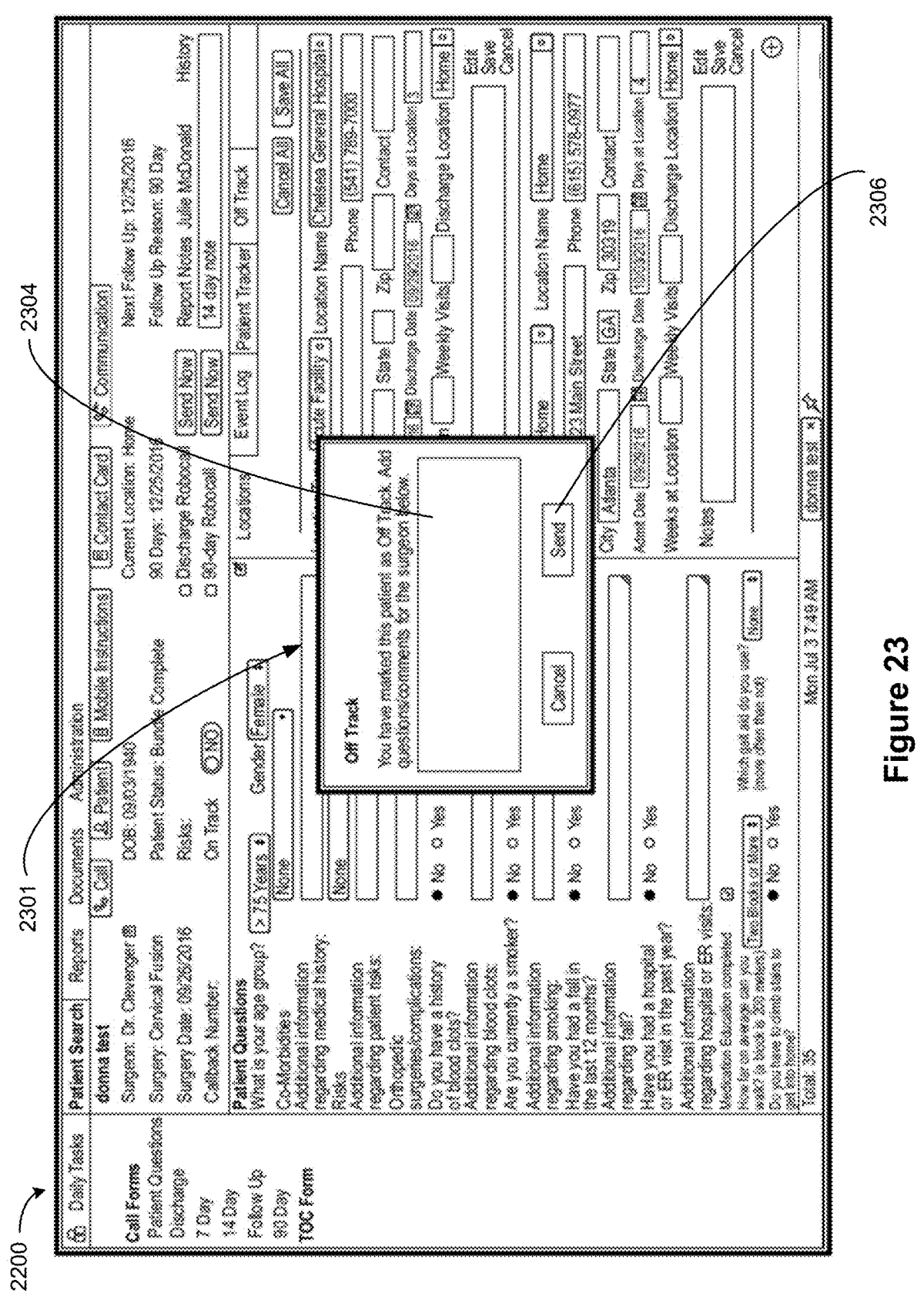
Figure 24:
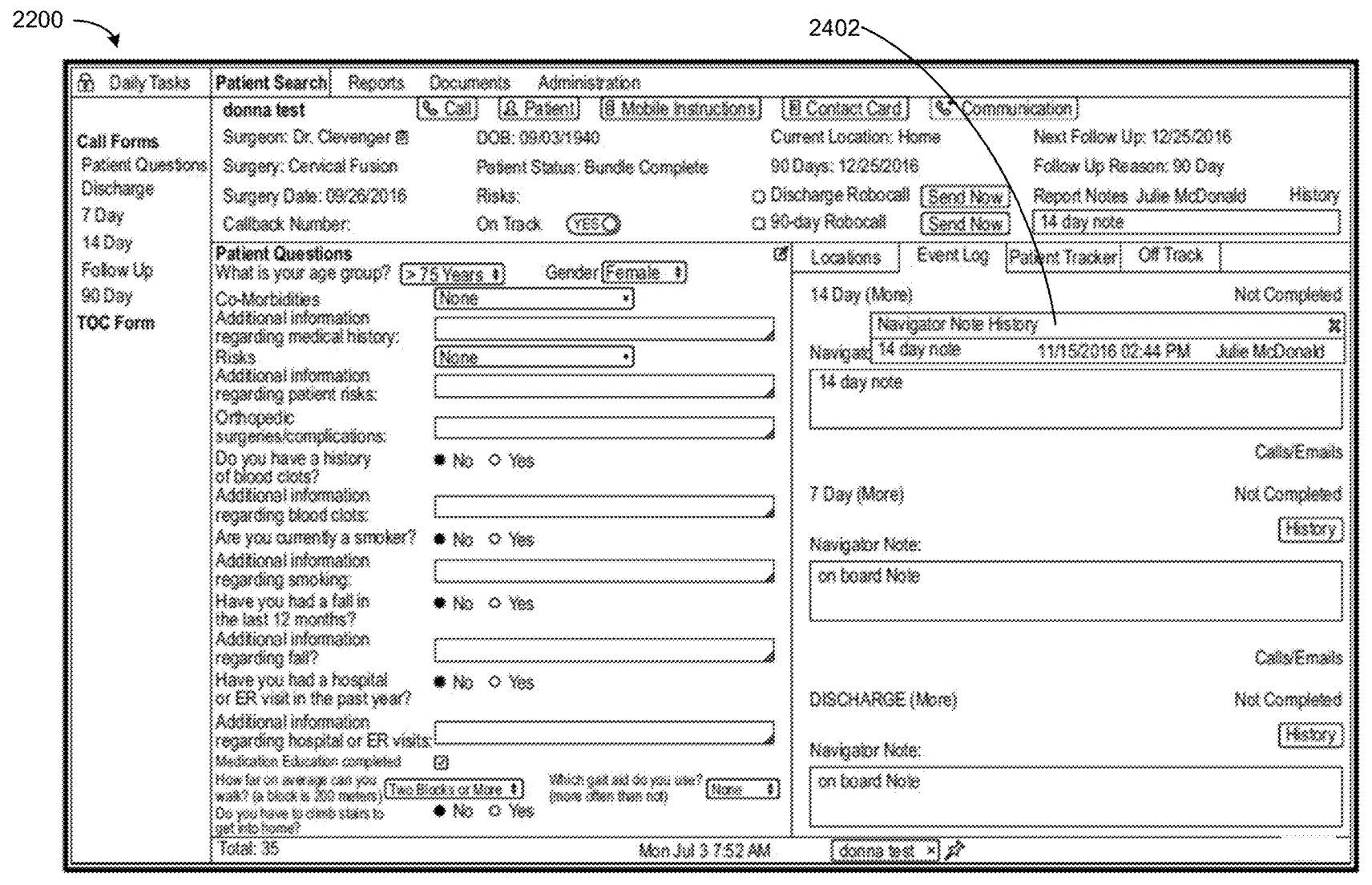

In FIG. 22, a patient information user interface 2200 is displayed. In some embodiments, in response to a tracking alert (e.g., received by management device 300 from server 200), an alert window 2301 is displayed (e.g., overlayed over patient information user interface 2200), as shown in FIG. 23. In some embodiments, alert window 2301 includes an off track message 2302, a response input field 2304, and/or a control 2306 that, when activated, causes the device to transmit input entered in the response input field to a remote device (e.g. a manager device 300 with manager interfaces 322, server 200, and/or user device 100). For example, the input entered in the response input field 2304 is displayed in a manager interface 322. In FIG. 24, note history indicator 2402 (e.g., including input entered in response input field 2304) is displayed overlayed over patient information user interface 2200 (e.g., in response to activation of control 2306).

Figure 25:
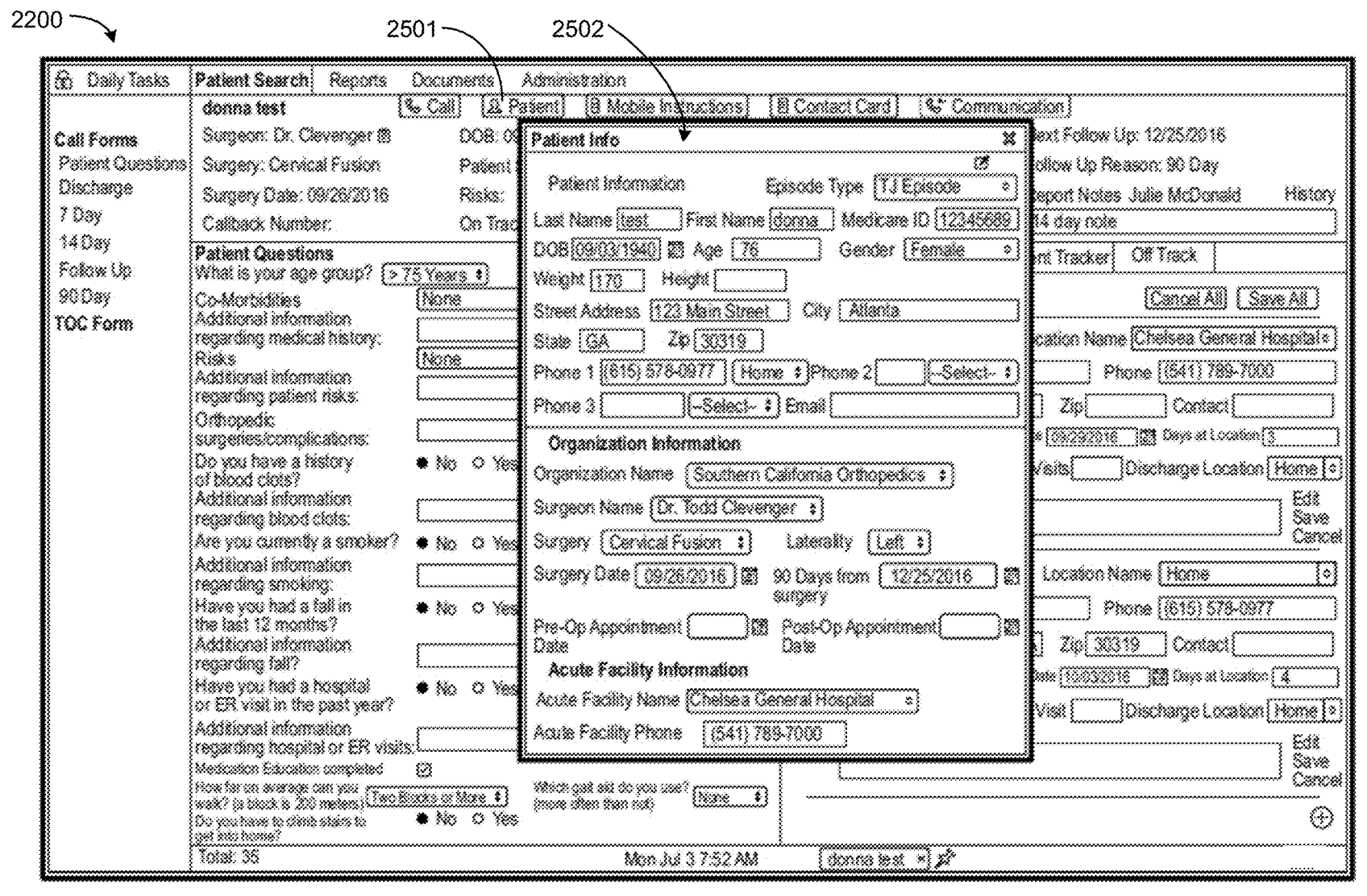

In FIG. 25, a patient information prompt window 2502 is displayed overlayed over patient information user interface 2200 (e.g., in response to input received at patient tab 2501). In some embodiments, information for one or more of identifying information 404, event information 406, indicated areas 408, and/or user manager information 424 of tracking program 118 is generated based on input entered in one or more fields of the patient information user interface 2200. For example, identifying information 404 is generated based on input entered in, for example, Last Name, First Name, Medicare ID, and/or DOB fields of the patient information user interface 2200.

Figure 26:
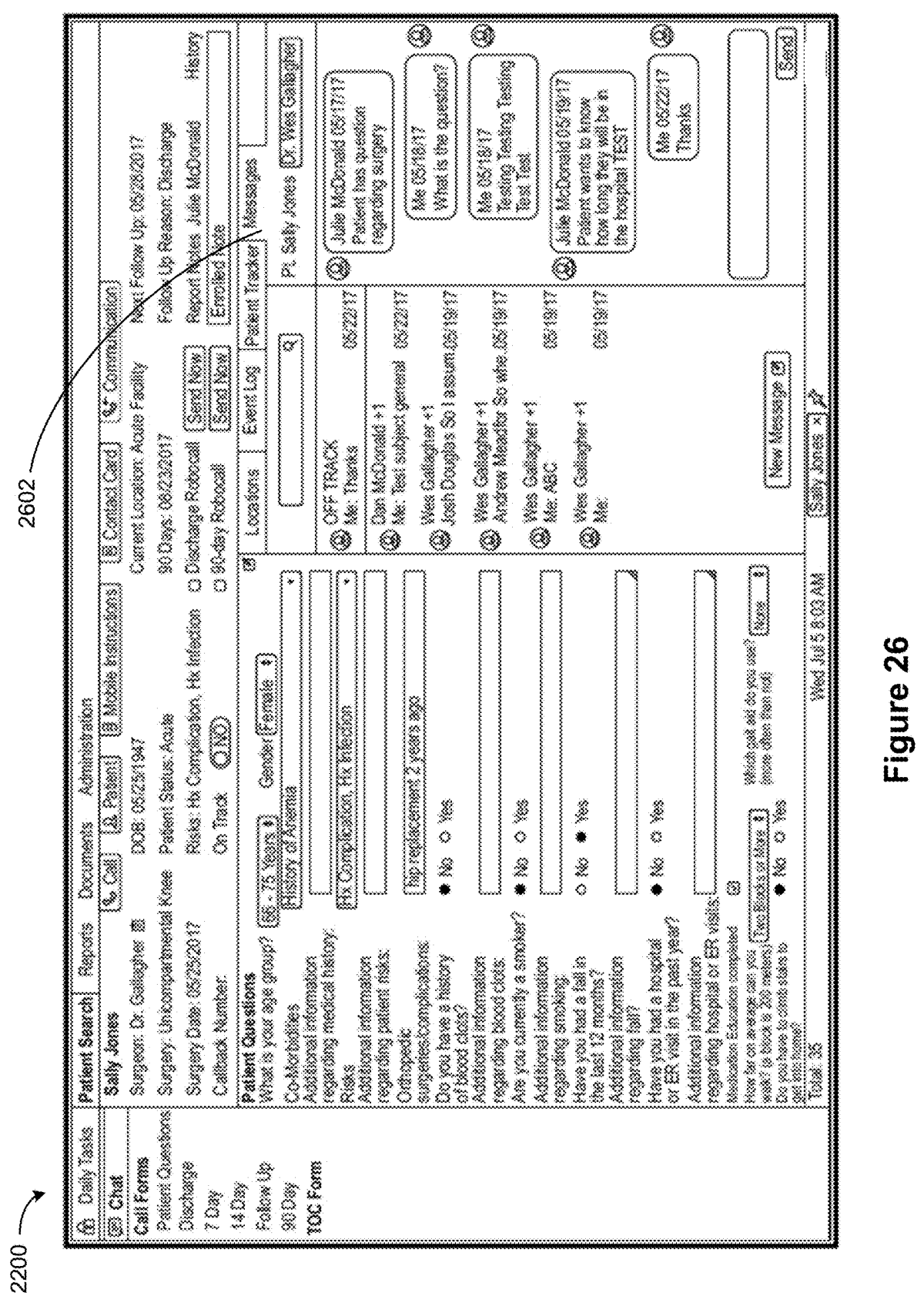

In FIG. 26, a messaging interface 2602 is displayed at a location that corresponds to (e.g., within) patient information user interface 2200 (e.g., in response to an input received at a messages tab of the patient information user interface). The messaging interface 2602 allows a sub-manager to communicate directly with a manager and/or a user.

Figure 27:
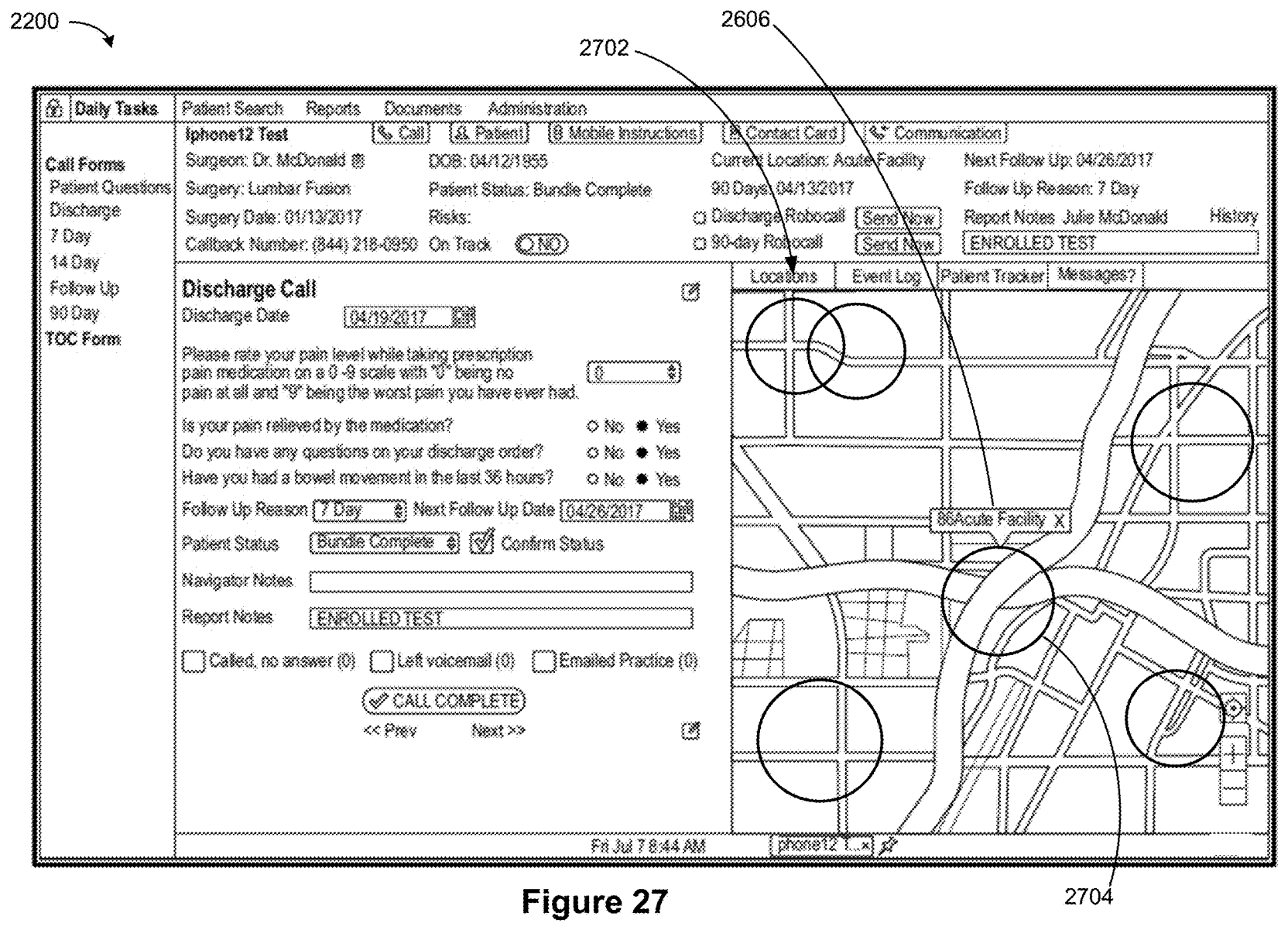

In FIG. 27, a patient tracker interface 2702 is displayed at a location that corresponds to (e.g., within) patient information user interface 2200 (e.g., in response to an input received at a patient tracker tab of the patient information user interface). The tracked user device map 2702 displays one or more geofences (e.g., geofence 2704) for one or more areas (e.g., indicated areas 408 for a currently selected user and/or all locations 222 within a current map view). In some embodiments, in response to an input detected at a location that corresponds to a geofence, identifying information 2706 for an indicated area is displayed.

Figure 28:
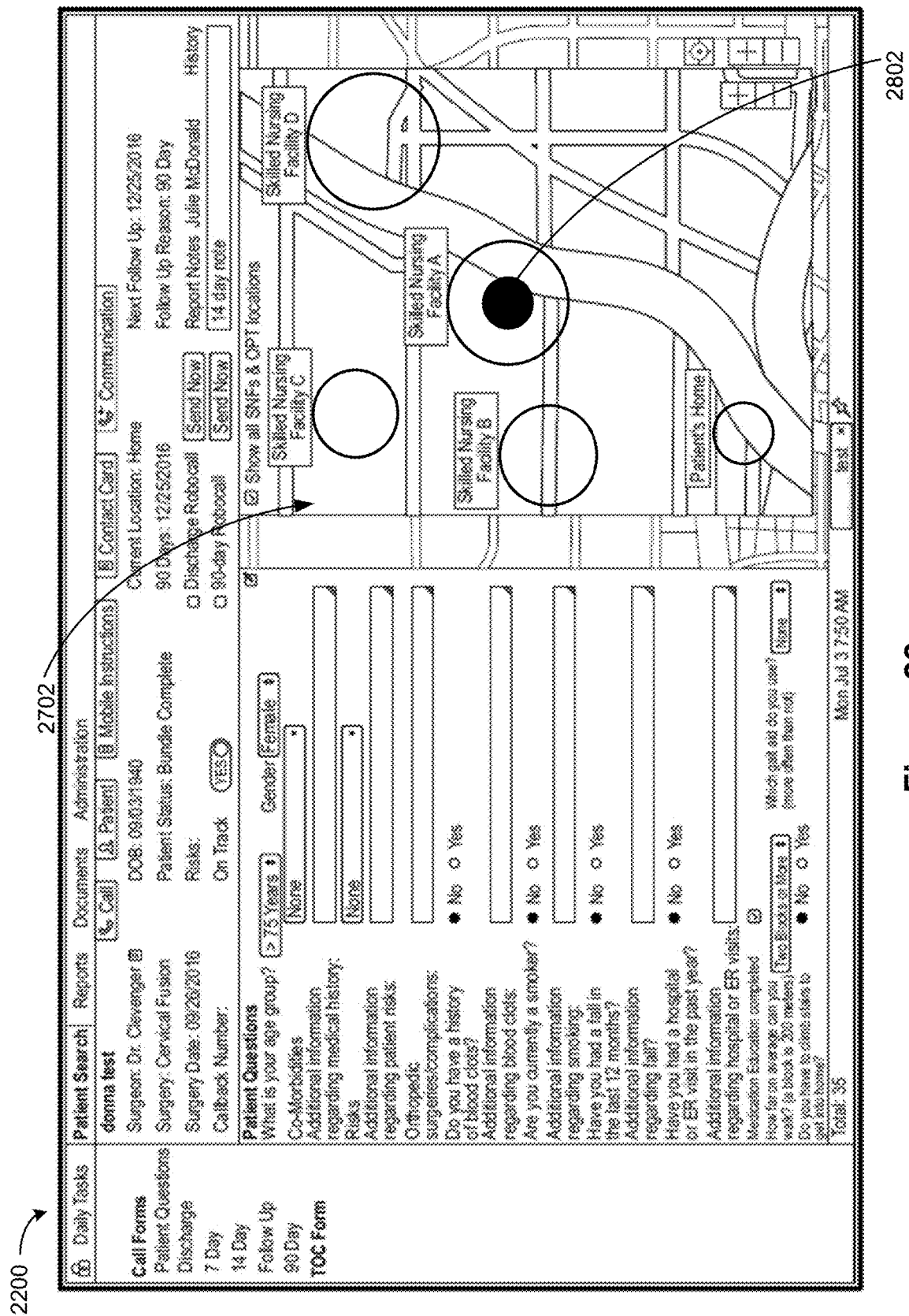

FIG. 28 illustrates a patient tracker user interface 2702 that indicates a determined location 2802 of a currently selected user. The determined location 2802 of the currently selected user is indicated by, for example, an altered ring color, an indicator displayed within a ring, and/or a text label.

Figure 29:
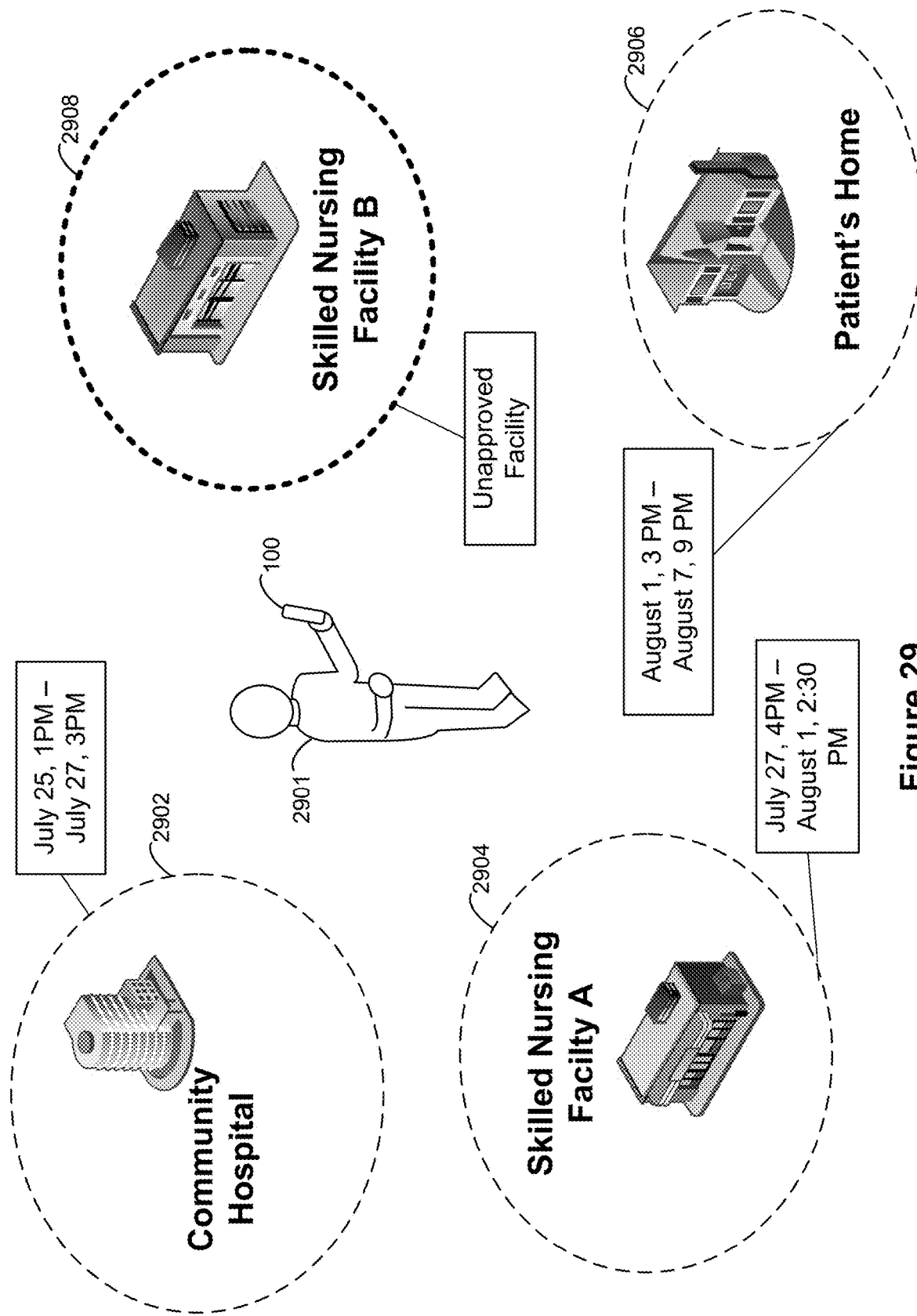
FIG. 29 illustrates a plurality of geofences that correspond to a tracking program, in accordance with some embodiments.

FIG. 29 is a diagram that illustrates a plurality of geofences (2902, 2904, and 2906) that correspond to a tracking program 118. For example, a tracking program 118 for user 2901 indicates that user 2901 is to be located at a first indicated area ("Community Hospital") for a first time period (e.g., from July 25 at 1:00 PM to July 27 at 3:00 PM), user 2901 is to be located at a second indicated area ("Skilled Nursing Facility A") for a second time period (e.g., from July 27 at 4:00 PM to August 1 at 2:30 PM), and user 2901 is to be located at a third indicated area ("Patient's Home") for a third time period (e.g., from August 1 at 3:00 PM to August 7 at 9:00 PM). The tracking program 118 also indicates that the facility "Skilled Nursing Facility B" is an unapproved location for user 2901 (e.g., the facility is not covered by the user's insurance).

At a time during the first time period (e.g., periodically during the first time period), user device 100 transmits location information determined by position determination module 117 to server 200. Server 200 determines (e.g., using position determination module 228) whether user device 100 is located within geofence 2902 that corresponds to the first location. In some embodiments, in accordance with a determination that user device 100 is not located within geofence 2902, an alert is generated (e.g., by alert generation module 230). In some embodiments, in accordance with a determination that user device is located within a geofence (e.g., 2904, 2906, or 2908) that is not geofence 2902, an alert is generated.

At a time during the second time period (e.g., periodically during the second time period), user device 100 transmits location information determined by position determination module 117 to server 200. Server 200 determines whether user device 100 is located within geofence 2904 that corresponds to the second location. In some embodiments, in accordance with a determination that user device 100 is not located within geofence 2904, an alert is generated (e.g., by alert generation module 230). In some embodiments, in accordance with a determination that user device is located within a geofence (e.g., 2902, 2906, or 2908) that is not geofence 2904, an alert is generated.

In some embodiments, during the first period, the second period, and/or the third period (e.g., during the entire period of time associated with the tracking program 118), user device 100 transmits location information determined by position determination module 117 to server 200. Server 200 determines whether user device 100 is located within geofence 2908 that corresponds to the unapproved location. In some embodiments, in accordance with a determination that user device 100 is located within geofence 2908, an alert is generated (e.g., by alert generation module 230).

Figure 30:
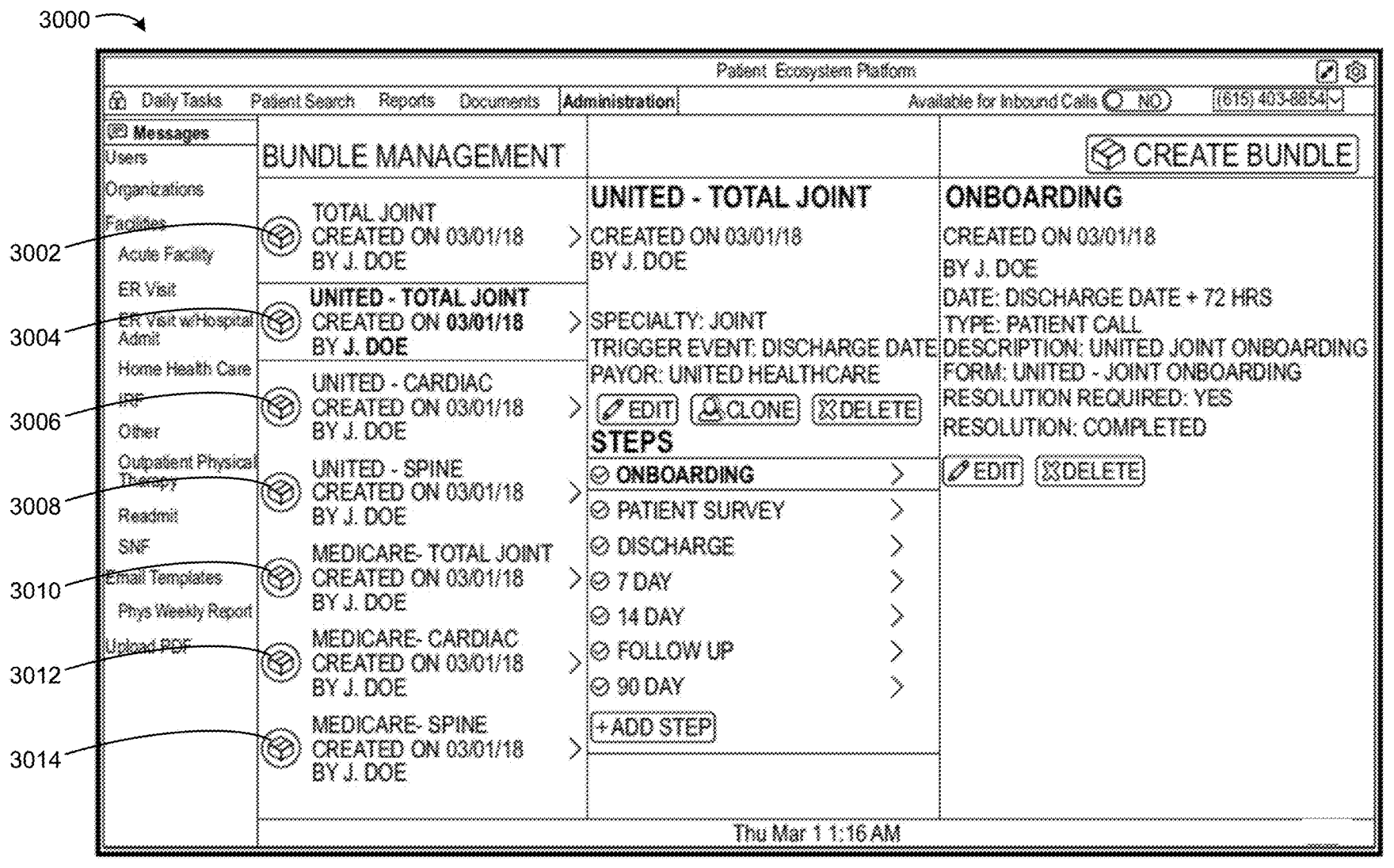

FIG. 30 illustrates a bundle management interface 3000 (e.g., displayed by management device 300), in accordance with some embodiments. Bundle management interface 3000 includes a list of selectable preconfigured bundles 3002-3014. In some embodiments, bundle management interface 3000 is used to generate a tracking program 118 for a user 2901. For example, one or more options for a first indicated area 410, a first time period 412, a second indicated area 416, a second time period 418 are associated with a bundle (e.g., based on procedure type, insurance, physician preference, patient type, and/or patient preference). Selecting a bundle reduces the time required to generate a tracking program 118 and/or limits the selectable options for tracking program 118 based on parameters associated with the bundle.

FIG. 31 illustrates a step creation user interface 3100 (e.g., displayed by management device 300) for creating and/or adjusting a step that is associated with a respective bundle. Step creation interface includes an alert type field 3102. A drop down menu 3104 displays options (e.g., display prompt for navigator patient call, robo patient call, SMS Message) available for the alert type field.

Figure 32:
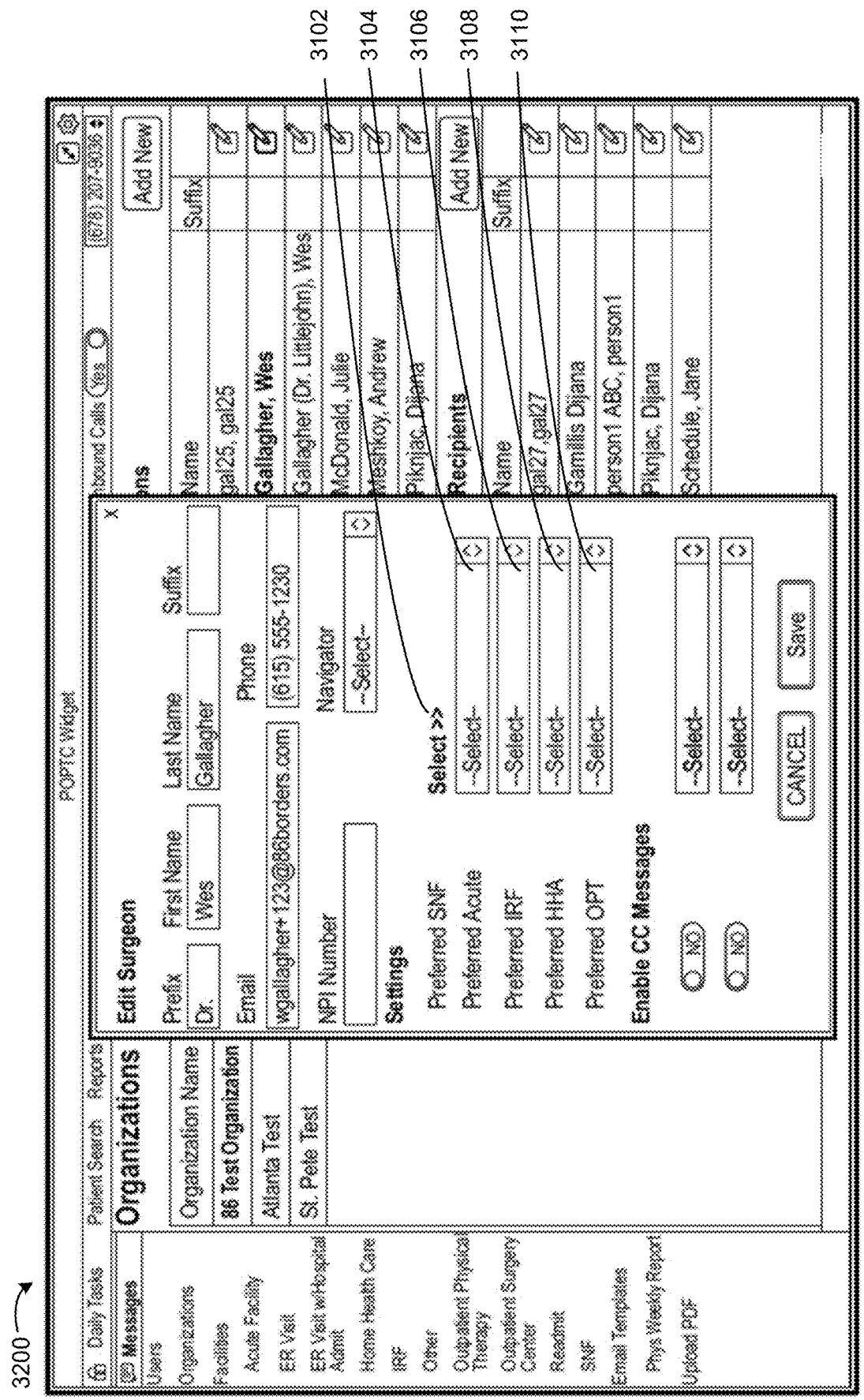
FIG. 32 illustrates a physician preference user interface, in accordance with some embodiments.

FIG. 32 illustrates a physician preference user interface 3200 (e.g., displayed by management device 300) usable to indicate one or more preferred options (e.g., to be associated with a bundle type and/or with bundles for the physician). For example, a physician uses facility selection fields 3202-3210 to select one or more preferred facilities (e.g., facilities where the physician practices).

FIG. 33 illustrates a facility selection user interface 3300 (e.g., displayed in response to an input that selects a control that corresponds to facility selection field 3202). Facility selection user interface 3300 includes controls (e.g., radius, rating, price) for filtering a set of available facility options (e.g., to produce a list of preferred options).

Figure 34:
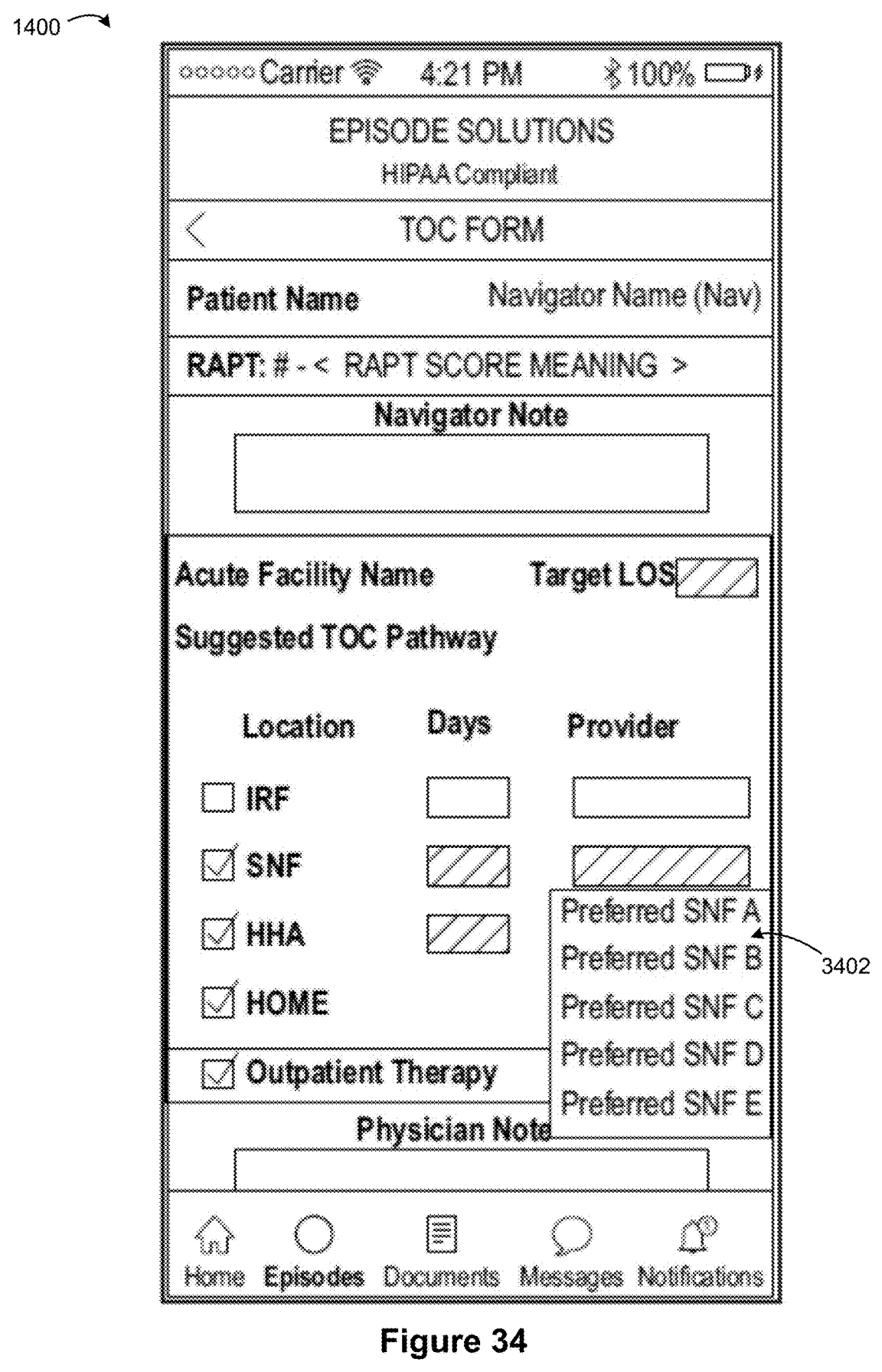

FIG. 34 illustrates a tracking program form 1400 (see FIG. 14) that is displaying a facility selection drop-down menu 3402 that is populated with a list of SNF facility options that meet selection criteria (e.g., as described with regard to FIGS. 32-33). In some embodiments, the facility selection drop-down menu 3402 is used to input an indicated area (e.g., first indicated area 410) of a tracking program 118.

Figure 35:
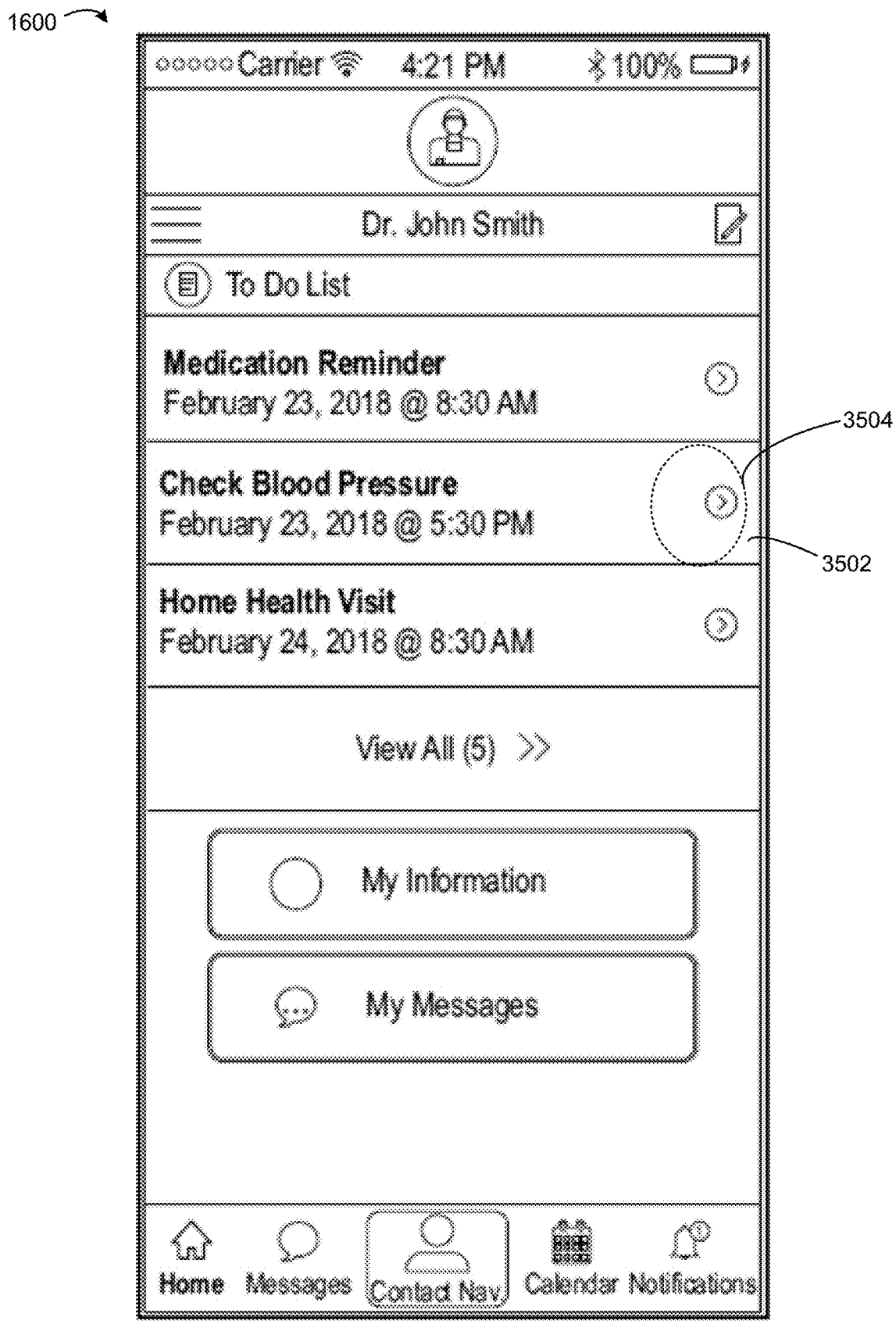
FIG. 35 illustrates a user portal home page, in accordance with some embodiments.

FIG. 35 illustrates a user portal home page 1600 (e.g., as described with regard to FIG. 16) that includes a measurement prompt 3502 ("Check Blood Pressure"). For example, measurement prompt 3502 is displayed to a patient when a measurement to be performed by the patient is included in tracking program 118.

Figure 36:
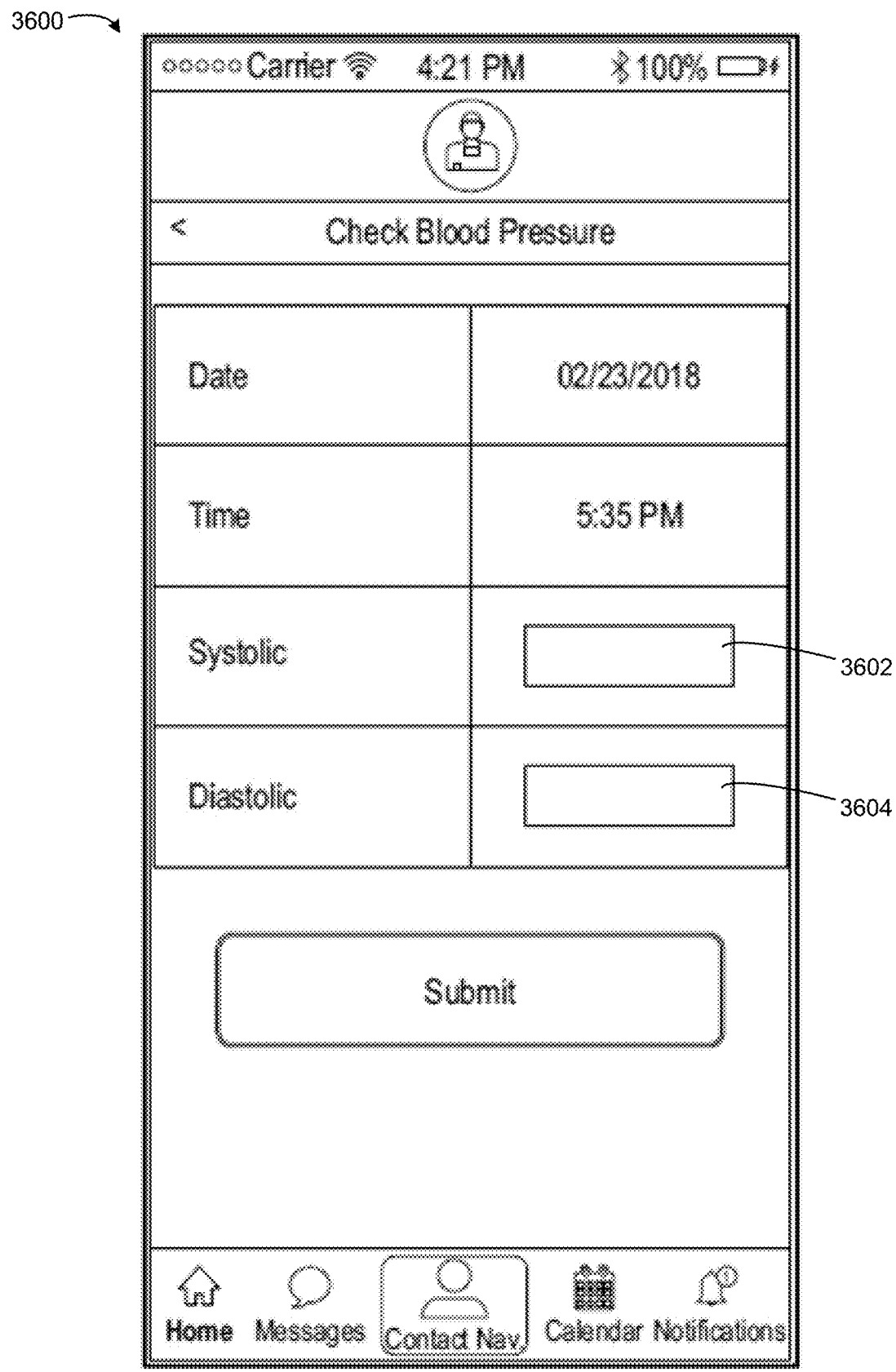
FIG. 36 illustrates a measurement interface, in accordance with some embodiments.
Figure 37B:
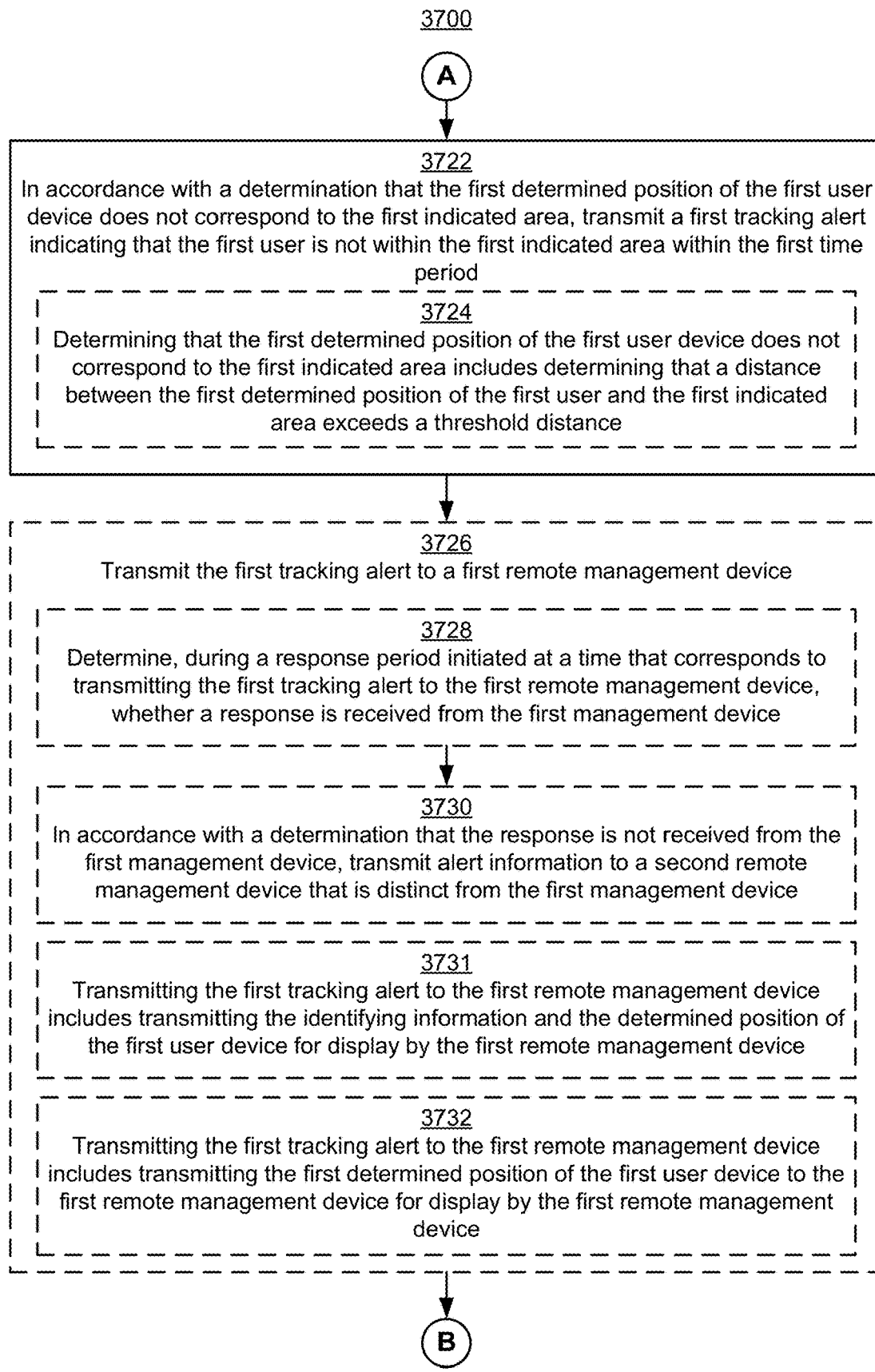
Figure 38C:
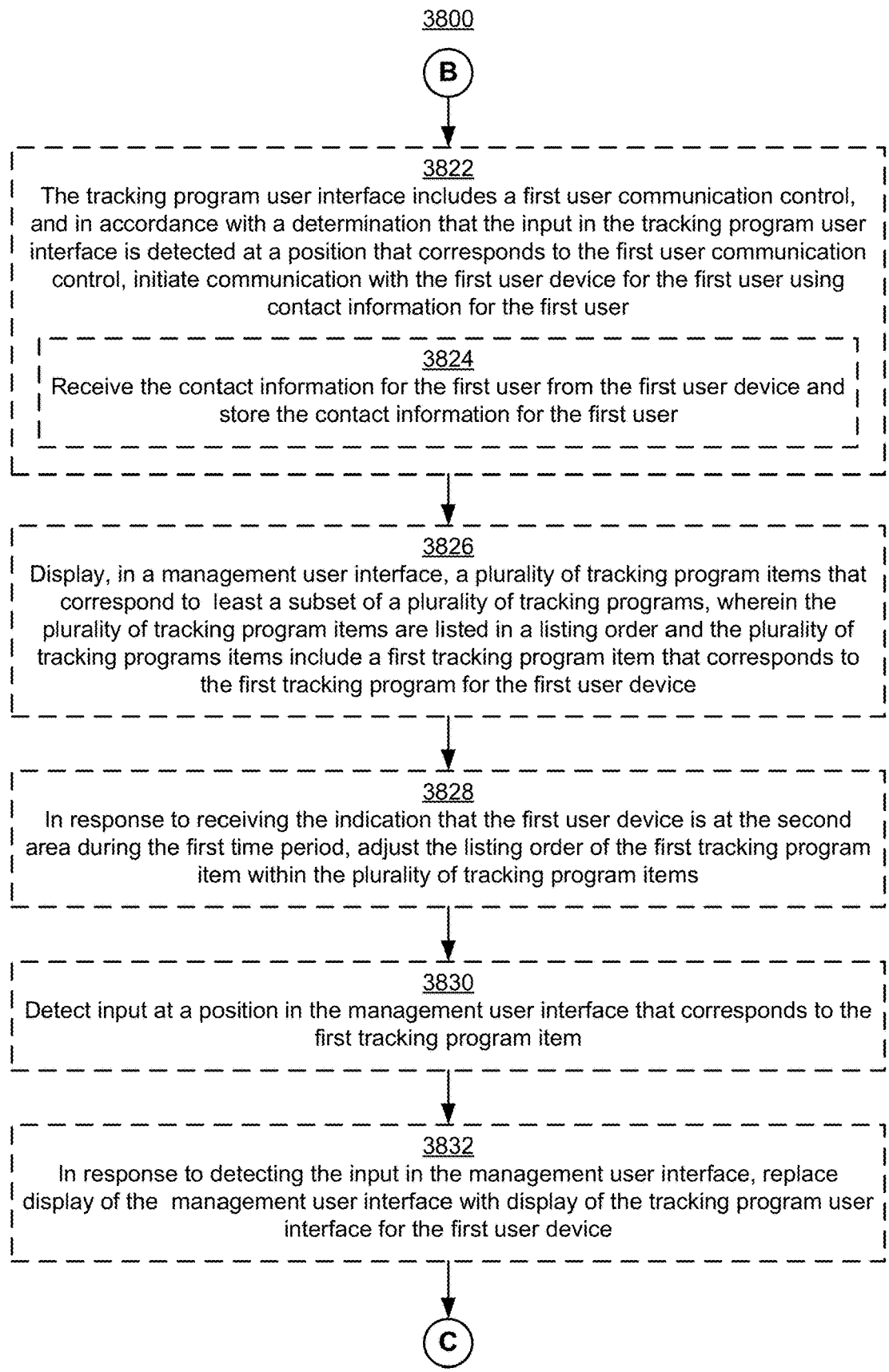
Figure 38D:
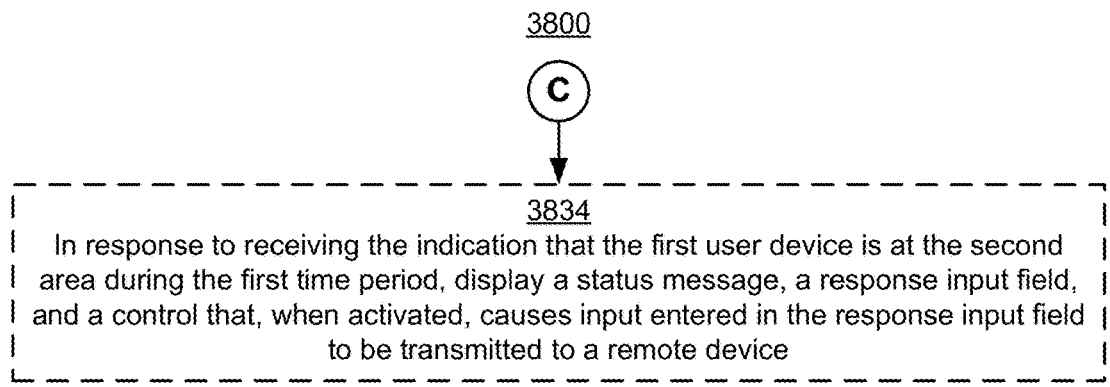

FIG. 36 illustrates a measurement interface 3600 (e.g., displayed in response to input 3504 that selects the measurement prompt 3502). User measurement information (e.g., systolic pressure and diastolic pressure) is provided via user input into fields (e.g., systolic input field 3602 and diastolic input field 3604) of measurement interface 3600.

FIGS. 37A-37D are flow diagrams illustrating a method 3700 for tracking a user, in accordance with some embodiments. The method 3700 is performed at a device, such as server 200. For example, instructions for performing the method 3700 are stored in the memory 204 and executed by the processor(s) 202. In some embodiments, part or all of method 3700 is performed at a user device 100 and/or a management device 300 (e.g., instructions for performing part or all of the method 3700 are stored in memory 104 and/or 304 and executed by processor(s) 102 and/or 302).

The device receives (3702) data for a first user including a first identifier associated with the first user (e.g., identifying information 404, such as user contact information and/or device identifying information) transmitted by a tracking application 116 on user device 100. For example, the data transmitted by tracking application 116 is user input provided via a user interface such as 1604. In some embodiments, the device receives data (e.g., identifying information 404, first indicated area 410, first time period 412, second indicated area 416, second time period 418, user manager 426, user sub-manager 428, and/or location 222) transmitted by a tracking management application 314 on management device 300. For example, the data transmitted by tracking management application 314 is user input provided via a user interface such as transition of care (TOC) form approval interface 1300 and/or TOC sub-manager interface 2300 (e.g., patient information prompt 2302) and/or 2400.

The device generates and stores (3704) a first tracking program 118a for the first user (e.g., in tracking program storage 216). The first tracking program 118a includes the first identifier associated with the first user (e.g., identifying information 404), a first indicated area (e.g., first indicated area 410) for the first user device 100 associated with the first user, and a first time period when the first user is scheduled to be located within the first indicated area (e.g., first time period 412). In some embodiments, the first tracking program 118a is a TOC program for a patient that indicates one or more designated locations (indicated areas) for patient care following a procedure and a designated period of time that the patient will spend at each designated location.

At a first time that corresponds to the first time period 412 (e.g., a time during the first time period 412, such as a start time of the first time period 412 or time that is a predetermined amount of time after the start time of the first time period 412), the device determines (3706), from a position detection system (e.g., position determination module 118 and/or position sensor 114) in the first user device 100, a first determined position of the first user device 100. In some embodiments, detecting the first determined position of the first user device 100 includes receiving position data (3708) from a remote monitoring device (e.g., user device 102). In some embodiments, the position detection system includes (3710) a positioning sensor (e.g., position sensor 114) of the remote monitoring device (e.g. user device 102).

In some embodiments, during the first time period 412, the device periodically (e.g., once per day, once per hour, once per ten minutes, or once per five minutes) determines (3712) positions of the first user device 100. In some embodiments, a rate at which the position of first user device 100 is determined is altered, e.g., in response to a command from a management device 300, in response to input detected at user device 100, and/or in response to a determination that a current time corresponds to an indicated time period (e.g., first time period 412, second time period 418). Allowing the rate at which the position of first user device 100 to be altered allows power consumption at first user device 100 for tracking to be controlled based on the tracking preferences of the user of first user device 100 and/or a user manager 424 or user sub-manager 426.

In some embodiments, the first time period 412 includes (3714) a designated start time (e.g., a time, date, and/or number of days after an event that a user is expected to move to the first indicated area, such as a first care facility).

In some embodiments (3716), the first time that corresponds to the first time period 412 is a predetermined time (e.g., a number of hours and/or days) after the designated start time.

In some embodiments, the first time period 412 includes (3718) a designated stop time (e.g., a number of days after the start time and/or a time and/or date when the first user is expected to leave the first indicated area). In some embodiments, the designated start time and the designated stop time are used to determine an actual utilization of the first indicated area.

The device compares (3720) the first determined position of the first user device 100 with the first indicated area 410.

In accordance with a determination that the first determined position of the first user device 100 does not correspond to the first indicated area 410, the device transmits (3722) a first tracking alert (e.g., an alert generated by alert generation module 230) indicating that the first user is not within the first indicated area within the first time period. For example, a transmitted tracking alert received by management device 300 is displayed in an alert display area 502 of manager user interface home page 500. In some embodiments, a transmitted tracking alert is received by a management device 300 of a sub-manager and is displayed in a sub-manager user interface, such as task user interface 2100 and/or patient information user interface 2200.

In some embodiments, the device determines one or more actual arrival times at which first user device 100 arrives at a first indicated area 410 and one or more actual departure times at which the first user device 100 departs from the first indicated area 410. For example, the device sets an arrival timestamp when a user device 100 is at a location that corresponds to a geofenced area and sets a departure timestamp when a user device 100 ceases to be at the location that corresponds to the geofenced area. In some embodiments, actual arrival times and/or actual arrival departure times are tracked to determine an amount of time (e.g., during a particular time period) that a user of first device 100 (e.g., a patient receiving post-surgery care and/or a caretaker visiting a patient post-surgery to provide care services) is present at an indicated area.

In some embodiments, the actual arrival time(s) and the actual departure time(s) are used to determine an actual utilization of the first indicated area and/or a service provided at a first indicated area. In some embodiments, an expected utilization fee is determined using the actual utilization of the first indicated area, the actual utilization determined for any additional indicated areas, and/or the actual utilization of a service provided at an indicated area. The expected utilization fees are compared to one or more assessed utilization fees. In this way, utilization and/or service overcharges can be determined based on a designated start time, a designated stop time, an actual arrival time, and/or an actual departure time. For example, if a user was present in a skilled nursing facility for a period of seven days, but the skilled nursing facility assessed utilization fee for the user is based on an 8-day stay, the actual arrival time and actual departure time determined using position signals from first user device 100 are usable to challenge and/or automatically reduce the inaccurate utilization fee. In another example, if a user was scheduled to receive home care for eight hours in a day, but a first user device 100 carried by the service provider was only at a location that corresponded to the patient's home for three hours in that day, one or more actual arrival times and actual departure times determined using position signals from first user device 100 are usable to challenge and/or automatically reduce a utilization fee based on an eight-hour visit.

In some embodiments, determining that the first determined position of the first user device 100 does not correspond to the first indicated area includes (3724) determining that a distance between the first determined position of the first user and the first indicated area exceeds a threshold distance.

In some embodiments, the device transmits (3726) the first tracking alert (e.g., an alert generated by alert generation module 230) to a first remote management device 300. For example, the first tracking alert is transmitted to a management device of a user manager 426 and/or a management device 300 of a user sub-manager 428. In some embodiments, a user interface displayed by the first remote management device 300 (e.g., manager user interface home page 500 and/or patient information user interface 2200) displays tracking alerts and/or tracking program information for at least one additional user that is distinct from the first user.

In some embodiments, the device determines (3728), during a response period initiated at a time that corresponds to transmitting the first tracking alert to the first remote management device, whether a response is received from the first management device 302 (e.g., a management device 300 of a manager to which multiple sub-managers report, such as a management device 300 that includes manager interface(s) module 322). In accordance with a determination that the response is not received from the first management device, the device transmits (3730) alert information to a second remote management device that is distinct from the first management device (e.g., a management device 300 that includes sub-manager interface(s) 324). For example, in some embodiments, one or more nurses that use management devices 300 that include sub-manager interface(s) module 322 report to a surgeon that has a management device 300 that includes manager interface(s) 322.

In some embodiments, transmitting the first tracking alert to the first remote management device 300 includes transmitting (3731) the identifying information 404 and the determined position of the first user device 100 for display by the first remote management device.

In some embodiments, transmitting the first tracking alert to the first remote management device 300 includes transmitting (3732) the first determined position of the first user device 100 to the first remote management device 300 for display (e.g., by output device 332) by the first remote management device 300.

In some embodiments, the first tracking program 118*a* includes (3734) a second indicated area 416 for the first user device 100 and a second time period 418 when the first user is scheduled to be located within the second indicated area. At a second time that corresponds to the second designated time period 418 (e.g., a time that is during the second designated time period 418, such as a start time of the second designated time period 418 or a time that is a predetermined amount of time after a start time of the second designated time period 418), the device determines (3736), from the position detection system (e.g., position determination module 118 and/or position sensor 114), a second determined position of the first user device 100. In some embodiments, the second time period 418 is distinct from the first time period 412 (e.g., a start time of the second time period 418 is equal to or later than an end time of the first time period 412). The device compares (3738) the second determined position of the first user device with the second indicated area 416. In accordance with a determination that the second determined position of the first user device 100 does not correspond to the second indicated area, the device transmits (3740) a second tracking alert (e.g., an alert generated by alert generation module 230) indicating that the first user is not within the second indicated area within the second time period.

In some embodiments, the device receives (3742) data for a second tracking program 118*b* for a second user device of a second user. The device stores (3744) the received data in the second tracking program 118*b* for the second user device.

In some embodiments, the first tracking program for the first user device includes (3746) identifying information for a remote service provider device (e.g., a device of a health care provider scheduled to meet with the first user, such as a nurse who visits the first user at the first user's home). For example, when an indicated area 408 (e.g., first indicated area 410) is the user's home, the user device, the service provider device, or both are tracked to determine if services are being provided in accordance with a tracking program 118*a* for the user. In some embodiments, the service provider device is a device 100 as described with regard to FIG. 1, and the service provider device is distinct from a user device 100 of a user receiving health services from the service provider.

In some embodiments, at a second time that corresponds to the first time period (e.g., a second time that is the same as the first time or a second time that is distinct from the first time), the device (e.g., the server 200) determines, from a position detection system in the remote service provider device, a first determined position of the remote service provider device. The device compares the first determined position of the remote service provider device with the first indicated area. In accordance with a determination that the first determined position of the remote service provider device does not correspond to the first indicated area, the device transmits a service provider alert indicating that the service provider device is not within the first indicated area within the first time period. For example, if a service provider misses an appointment with the first user, is present for a period of time that is shorter than an expected period of time, and/or is present for a period of time that is longer than an expected period of time, a notification is made available (e.g., for viewing on a manager and/or sub-manager device).

In some embodiments, the device determines (3748) a set of locations that meet selection criteria. In some embodiments, the set of locations includes one or more locations that correspond to a respective bundle (e.g., bundle 3002). In some embodiments, the set of locations includes one or more predetermined preferred locations (e.g., indicated via input received at physician preference user interface 3200 and/or facility selection user interface 3300). In some embodiments, a location meets the selection criteria when the location complies with user insurance requirements, when the location is indicated as a preferred location of a physician and/or user, when the location is within a predetermined and/or specified distance of an indicated location, when the location meets a predetermined and/or specified quality rating, and/or when the location falls within a predetermined and/or specified price range. In some embodiments, the first indicated area 410 and/or a second indicated area 416, etc. are selected from the set of locations.

In some embodiments, the tracking program includes (3750) a first indicated measurement (e.g., blood pressure, blood analysis, heart rate, and/or weight) and a measurement time period when the first indicated measurement is to be performed. For example, as described with regard to FIG. 35, an indicated measurement is a blood pressure measurement to take place on Feb. 23, 2018 at 5:30 PM. At a measurement time that corresponds to the measurement time period, the device determines whether the first indicated measurement has been performed. For example, the device determines whether measurement input (e.g., input entered via measurement interface 3600) is received from user device 100. In accordance with a determination that the first indicated measurement has not been performed, the device transmits a measurement alert indicating that the first indicated measurement has not been performed.

In some embodiments, at the first time that corresponds to the first time period, the device compares (3752) the first determined position of the first user device 100 with an unapproved area (e.g., as described with regard to FIG. 4). For example, as described with regard to FIG. 29, the device (e.g., server 200) determines whether user device 100 is within the unapproved area bounded by geofence 2908. In accordance with a determination that the first determined position of the first user device corresponds to the unapproved area, the device transmits a second tracking alert indicating that the first user is within the unapproved area within the first time period.

In some embodiments, the first tracking program includes (3754) the unapproved area.

FIGS. 38A-38D are flow diagrams illustrating a method 3800 for communicating with a communication target when a first user device 100 is not at an indicated area, in accordance with some embodiments. The method 3800 is performed at a device, such as management device 300. For example, instructions for performing the method 3800 are stored in the memory 304 and executed by the processor(s) 302 of the management device 300. In some embodiments, part or all of method 3800 is performed at a user device 100 and/or a server device 200 (e.g., instructions for performing part or all of the method 3800 are stored in memory 104 and/or 204 and executed by processor(s) 102 and/or 202).

The device receives (3802), by the input device (e.g., an input device 330 of I/O module 308), data for a first tracking program 118*a* for a first user device 100 of a first user. The received data for the first tracking program 118*a* for the first user device 100 includes a first identifier (e.g., identifying information 404) associated with the first user, a first indicated area 410 for the first user device 100, and a first time period 412 that corresponds to the first indicated area 410. In some embodiments, the device receives the data for the first tracking program 118*a* via a tracking management application 314 on management device 300. For example, data for the first tracking program 118*a* is provided via a user interface such as transition of care (TOC) form approval interface 1300 and/or TOC sub-manager interface 2300 (e.g., patient information prompt 2302) and/or 2400.

The device transmits (3804), to a remote server 200, the received data for the first tracking program 118*a* for the first user device.

During the first time period 412, the device receives (3806), from the remote server 200, an indication that the first user device 100 is at a second area, distinct from the first indicated area 410. In some embodiments, the indication that the first user device 100 is at a second area is based on a determination that the first user is not at the first indicated area 410. In some embodiments, the indication that the first user device 100 is at a second area is based on a determination that the first user is at a second indicated area 416.

The device displays (3808), on a display (e.g., output device 332), a tracking program user interface (e.g., a manager interface 322 and/or sub-manager interface 324, such as tracking program user interface 600) for the first user device. The tracking program user interface for the first user device includes a second area communication control (e.g., control 602 and/or 604), that, when activated, initiates communication with a second area communication target. For example, in FIG. 600, the first user device 100 is at a second area that is a skilled nursing facility "SNF (Brookdale)." The first indicated area 410 for the first user device 100 is the user's home (as indicated by the note "Off Track due to discharge location being SNF & not home." Control 602, when activated (e.g., by an input by input device 330, such as a tap input by a contact on a touchscreen display at a location that corresponds to control 602), causes the device to transmit a message (e.g., an automatically generated message) to communication target "SNF (Brookdale)" and/or causes the device to display a message interface for transmitting a message to communication target "SNF (Brookdale)." Control 604, when activated (e.g., by an input by input device 330, such as tap input by a contact on a touchscreen display of device 300 at a location that corresponds to control 604), causes the device to initiate a call to communication target "SNF (Brookdale)." In some embodiments, the tracking program user interface displays a control for sending an e-mail to the second area communication target. In some embodiments, a communication type (e.g., telephone call, text message, video call, and/or e-mail) and/or one or more communication addresses (e.g., telephone number, e-mail address) for the second area communication control are determined in accordance with an ordered list of communication types and/or designated communication address preferences (e.g., a preference list as indicated by a second area communication target, a user manager, and/or a user sub-manager, such as the preference list illustrated in FIG. 9). For example, if communication of a first communication type from the ordered list of communication types does not succeed, a second control of a second communication type from the ordered list of communication types is displayed. In some embodiments, multiple communication controls are displayed simultaneously, ordered in accordance with an ordered list of communication types and/or designated communication address preferences. In some embodiments, a second area communication target includes multiple contacts associated with the second area (e.g., a list of multiple text message and/or e-mail recipients). In some embodiments, the tracking program user interface displays an option to view at least a portion of the first tracking program for the first user. In some embodiments, the second area communication target includes a user device 100.

The device detects (3810), by the input device 330, an input at the tracking program user interface (e.g., user interface 600).

In accordance with a determination that the input is detected at a position that corresponds to the second area communication control (e.g., control 602 and/or control 604), the device initiates (3812) the communication with the second area communication target (e.g., "SNF (Brookdale)").

In some embodiments, contact information 420 for the second area communication target is included (3814) in the received indication that the first user device 100 is at the second area during the first time period 412.

In some embodiments, initiating the communication with the second area communication target includes automatically generating (3816) message text, replacing display of the tracking program user interface (e.g., user interface 600) with display of a messaging interface (e.g., user interface 1100) that includes a message input field 1104 and an address input field 1102, displaying the automatically generated message text in the message input field 1104; and populating the address field 1102 with the contact information for the second area communication target.

In some embodiments, initiating the communication with the second area communication target includes initiating (3818) a telephone call using a phone number included in the contact information for the second area communication target.

In some embodiments, in response to the receiving the indication that the first user device 100 is at the second area, the device determines (3820), using locally stored data (e.g., location data stored in memory 304), contact information for the second area communication target.

In some embodiments, the tracking program user interface (e.g., user interface 600) includes (3822) a first user communication control. In accordance with a determination that the input in the tracking program user interface is detected at a position that corresponds to the first user communication control, the device initiates communication with the first user device 100 using contact information for the first user.

In some embodiments, the device receives (3824), from the first user device 100, the contact information for the first user, and the device stores the contact information for the first user (e.g., in memory 304).

In some embodiments, the tracking program user interface (e.g., user interface 600) includes a sub-manager device communication control (e.g., 606 and/or 608). In accordance with a determination that the input in the tracking program user interface is detected at a position that corresponds to the sub-manager device communication control, the device initiates communication with the sub-manager device (e.g., a management device 300 that displays sub-manager user interface 324).

In some embodiments, the device displays (3826), in a management user interface, a plurality of episode records (e.g., 1202-1212) that correspond to at least a subset of a plurality of tracking programs 118. The plurality of tracking program items are listed in a listing order, and the plurality of tracking programs items include a first tracking program item (e.g., 1206) that corresponds to the first tracking program 118a for the first user device 100. In response to receiving the indication that the first user device 100 is at the second area during the first time period, the device adjusts (3828) the listing order of the first tracking program item 118a within the plurality of tracking program items (e.g., the positions of episode records 1202 and 1206 are adjusted such that 1206 is displayed above 1202 in the listing order). The device detects (3830) input at a position in the management user interface that corresponds to the first tracking program item 1206. In response to detecting the input in the management user interface, the device replaces display (3832) of the management user interface with display of the tracking program user interface (e.g., user interface 600) for the first user device.

In some embodiments, in response to receiving the indication that the first user device 100 is at the second area during the first time period 412, the device displays (3834) a status message (e.g., off-track message 612 or 2302), a response input field (e.g., 610 or 2304), and a control (e.g., 606 or 2306) that, when activated, causes the device to transmit input entered in the response input field to a remote device. For example, input received in response input field 2304 of sub-manager interface 2300 is transmitted to a manager device, and input received at response input field 610 of manager interface 600 is transmitted to a sub-manager device.

In some embodiments, a user is tracked without a tracking program 118. For example, a position of a first user device 100 is determined (e.g., periodically), and if a determined position of first user device 100 corresponds to a predetermined area (e.g., a geofenced area from a predetermined set of geofenced areas), a tracking alert is transmitted (e.g., to a management device 300). In this way, when a user self-refers to a facility (such as an emergency room), an alert is generated (e.g., so that a manager or sub-manager may contact the user and/or the facility). Determined positions of first user device 100 that do not correspond to a predetermined area (e.g., when the user visits a grocery store) are not stored and do not cause an alert to be generated.

Features of the present invention can be implemented in, using, or with the assistance of a computer program product, such as a storage medium (media) or computer readable storage medium (media) having instructions stored thereon/in which can be used to program a processing system to perform any of the features presented herein. The storage medium (e.g., memory 104, 204, 304) can include, but is not limited to, high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. Memory 104, 204, 304 optionally includes one or more storage devices remotely located from the CPU(s) 102, 202, 302. Memory 104, 204, 304 or alternatively the non-volatile memory device(s) within memory 104, 204, 304 comprises a non-transitory computer readable storage medium.

Stored on any one of the machine readable medium (media), features of the present invention can be incorporated in software and/or firmware for controlling the hardware of a processing system, and for enabling a processing system to interact with other mechanism utilizing the results of the present invention. Such software or firmware may include, but is not limited to, application code, device drivers, operating systems, and execution environments/containers.

Communication systems as referred to herein (e.g., communication system 108, 208, 308) optionally communicate via wired and/or wireless communication connections. Communication systems optionally communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. Wireless communication connections optionally use any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 102.11a, IEEE 102.11ac, IEEE 102.11ax, IEEE 102.11b, IEEE 102.11g and/or IEEE 102.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method for tracking a user device, comprising:
at one or more computing devices:
receiving data for a first user including a first identifier associated with the first user;
generating and storing a first tracking program for the first user, the first tracking program including:
the first identifier associated with the first user;
a first indicated area for a first user device associated with the first user; and
a first time period when the first user is scheduled to be located within the first indicated area, wherein the first time period includes a designated start time and a designated stop time;
after generating and storing the first tracking program and at the first time period when the first user is scheduled to be located within the first indicated area, determining, from a position detection system in the first user device, a first determined position of the first user device;
comparing the first determined position of the first user device with the first indicated area; and
in accordance with a determination that the first determined position of the first user device does not correspond to the first indicated area for a duration of the first time period, transmitting, to a first remote management device, a first tracking alert indicating that the first user is not within the first indicated area within the first time period;
determining whether a response is received from the first remote management device; and
in accordance with a determination that the response is not received from the first remote management device, transmitting alert information to a second remote management device that is distinct from the first remote management device.

2. The method of claim 1, wherein the first tracking program includes a second indicated area for the first user device and a second time period when the first user is scheduled to be located within the second indicated area, the method including:
at a second time that corresponds to the second time period, determining from the position detection system, a second determined position of the first user device;
comparing the second determined position of the first user device with the second indicated area; and
in accordance with a determination that the second determined position of the first user device does not correspond to the second indicated area, transmitting a second tracking alert indicating that the first user is not within the second indicated area within the second time period.

3. The method of claim 1, wherein the first tracking program for the first user device includes identifying information for a remote service provider device, the method further comprising:
at a second time that corresponds to the first time period, determining, from a position detection system in the remote service provider device, a first determined position of the remote service provider device;
comparing the first determined position of the remote service provider device with the first indicated area; and
in accordance with a determination that the first determined position of the remote service provider device does not correspond to the first indicated area, transmitting a service provider alert indicating that the remote service provider device is not within the first indicated area within the first time period.

4. The method of claim 1, including:
receiving data for a second user including a second device identifier associated with a second user device of the second user; and
generating and storing a second tracking program for the second user.

5. The method of claim 1, including:
determining, during a response period initiated at a time that corresponds to transmitting the first tracking alert to the first remote management device, whether the response is received from the first remote management device.

6. The method of claim 1, wherein transmitting the first tracking alert to the first remote management device includes transmitting identifying information to a remote service provider device and the determined position of the first user device for display by the first remote management device.

7. The method of claim 1, wherein transmitting the first tracking alert to the first remote management device includes transmitting the first determined position of the first user device to the first remote management device for display by the first remote management device.

8. The method of claim 1, wherein determining that the first determined position of the first user device does not correspond to the first indicated area includes determining that a distance between the first determined position of the first user and the first indicated area exceeds a threshold distance.

9. The method of claim 1, including:
during the first time period, periodically determining positions of the first user device comparing each of the periodically determined positions of the first user device with the first indicated area; and
in accordance with a determination that any of the periodically determined positions of the first user device does not correspond to the first indicated area during the first time period, transmitting, to the first remote management device, a second tracking alert indicating that the first user is not within the first indicated area.

10. The method of claim 1, wherein the designated start time includes a time and a date.

11. The method of claim 1, wherein:
a first time that corresponds to the first time period is a predetermined time after the designated start time; and
the step of determining the first determined position of the first user device occurs at the first time.

12. The method of claim 1, wherein the designated stop time occurs after the designated start time.

13. The method of claim 1, including:
determining a set of locations that meet selection criteria; and
wherein the first indicated area is selected from the set of locations.

14. The method of claim 1, wherein:
the tracking program includes a first indicated measurement and a measurement time period when the first indicated measurement is to be performed;
at a measurement time that corresponds to the measurement time period, determining whether the first indicated measurement has been performed; and
in accordance with a determination that the first indicated measurement has not been performed, transmitting a measurement alert indicating that the first indicated measurement has not been performed.

15. The method of claim 1, including:
at a first time that corresponds to the first time period:
comparing the first determined position of the first user device with an unapproved area; and
in accordance with a determination that the first determined position of the first user device corresponds to the unapproved area, transmitting a second tracking alert indicating that the first user is within the unapproved area within the first time period.

16. The method of claim 15, wherein the first tracking program includes the unapproved area.

17. The method of claim 1, wherein the first determined position of the first user device is determined at a first time during the first time period, the method further comprising:
determining, a second determined position of the first user device at a second time during the first time period, wherein the second time is an end time of the first time period; and
in accordance with a determination that the first and second determined position of the first user device does not correspond to the first indicated area, transmitting the first tracking alert.

18. A system, comprising:
memory;
one or more processors; and
one or more programs, wherein the one or more programs are stored in the memory and configured to be executed by the one or more processors, the one or more programs including instructions for:
receiving data for a first user including a first identifier associated with the first user;
generating and storing a first tracking program for the first user, the first tracking program including:
a first identifier associated with the first user;
a first indicated area for a first user device associated with the first user; and
a first time period when the first user is scheduled to be located within the first indicated area, wherein the first time period includes a designated start time and a designated stop time;
after generating and storing the first tracking program and at the first time period when the first user is scheduled to be located within the first indicated area, determining, from a position detection system in the first user device, a first determined position of the first user device;
comparing the first determined position of the first user device with the first indicated area; and
in accordance with a determination that the first determined position of the first user device does not correspond to the first indicated area for a duration of the first time period, transmitting, to a first remote management device, a first tracking alert indicating that the first user is not within the first indicated area within the first time period;
determining whether a response is received from the first remote management device; and
in accordance with a determination that the response is not received from the first remote management device, transmitting alert information to a second remote management device that is distinct from the first remote management device.

19. A non-transitory computer readable storage medium storing one or more programs, the one or more programs comprising instructions, which when executed by an electronic device, cause the device to:
receive data for a first user including a first identifier associated with the first user;
generate and store a first tracking program for the first user, the first tracking program including:
identifying information for the first user;
a first indicated area for a first user device associated with the first user; and
a first time period when the first user is scheduled to be located within the first indicated area, wherein the first time period includes a designated start time and a designated stop time;

after generating and storing the first tracking program and during the first time period when the user is scheduled to be located within the first indicated area, determine, from a position detection system in the first user device, a first determined position of the first user device;

compare the first determined position of the first user device with the first indicated area; and in accordance with a determination that the first determined position of the first user device does not correspond to the first indicated area for a duration of the first time period, transmit, to a first remote management device, a first tracking alert indicating that the first user is not within the first indicated area within the first time period;

determine whether a response is received from the first remote management device; and in accordance with a determination that the response is not received from the first remote management device, transmit alert information to a second remote management device that is distinct from the first remote management device.

\* \* \* \* \*